(12) United States Patent
Claps et al.

(10) Patent No.: US 7,679,745 B2
(45) Date of Patent: Mar. 16, 2010

(54) TIME-RESOLVED FLUORESCENCE SPECTROMETER FOR MULTIPLE-SPECIES ANALYSIS

(75) Inventors: Ricardo Claps, San Jose, CA (US); Bradley A. Smith, San Jose, CA (US)

(73) Assignee: Neptec Optical Solutions

( * ) Notice: Subject to any disclaimer, the term of this patent is extended or adjusted under 35 U.S.C. 154(b) by 491 days.

(21) Appl. No.: 11/603,939

(22) Filed: Nov. 21, 2006

(65) Prior Publication Data
US 2008/0117418 A1  May 22, 2008

(51) Int. Cl.
*G01J 3/30* (2006.01)
(52) U.S. Cl. ..................................... 356/417
(58) Field of Classification Search ................. 356/317, 356/417
See application file for complete search history.

(56) References Cited

U.S. PATENT DOCUMENTS

| | | | |
|---|---|---|---|
| 4,855,930 A | 8/1989 | Chao et al. | |
| 5,571,897 A | 11/1996 | Takalo et al. | |
| 5,701,012 A | 12/1997 | Ho et al. | |
| 5,895,922 A | 4/1999 | Ho et al. | |
| 5,990,484 A | 11/1999 | Ohsuka et al. | |
| 5,999,250 A | 12/1999 | Hairston et al. | |
| 6,159,686 A * | 12/2000 | Kardos et al. ................... | 435/6 |
| 6,455,861 B1 | 9/2002 | Hoyt et al. | |
| 6,532,067 B1 | 3/2003 | Chang et al. | |
| 6,858,852 B2 | 2/2005 | Wolleschensky et al. | |
| 6,870,165 B2 | 3/2005 | Amirkhanian et al. | |
| 6,947,134 B2 | 9/2005 | Chang et al. | |
| 7,113,282 B2 | 9/2006 | Aguirre et al. | |
| 2003/0116436 A1 * | 6/2003 | Amirkhanian et al. ...... | 204/452 |
| 2005/0260764 A1 | 11/2005 | Grigsby et al. | |
| 2006/0072110 A1 | 4/2006 | Lodder et al. | |
| 2006/0072873 A1 | 4/2006 | Tekippe et al. | |
| 2006/0132778 A1 * | 6/2006 | Curry et al. .................. | 356/417 |
| 2006/0142650 A1 | 6/2006 | Lodder et al. | |

OTHER PUBLICATIONS

Notification of Transmittal of the International Search Report in correspoding International Application No. PCT/US07/85132 Dated Jun. 26, 2008 (1 page).
Internatioanl Search Report in corresponding International Application No. PCT/US07/85132 dated Jun. 26, 2008 (2 pages).
Written Opinion of the International Searching Athority in corresponding Internaitonal Application No. PCT/US07/85132 dated Jun. 26, 2008 (7 pages).
Windig, W. et al. Applications and new devepolments of the direct exponential curve resolution algorithm (DECRA). Examples of spectra and magnetic resonance images. Journal of Chemometrics. Jul. 1999, vol. 13, No. 2, pp. 95-110, ISSN 1099-128X. Eq. 2, 6, 8-10; last paragraph in p. 96; section 2.2; para [3]; p. 103 (16 pages).

(Continued)

*Primary Examiner*—Kara E Geisel
(74) *Attorney, Agent, or Firm*—Haynes and Boone, LLP; Edward C. Kwok

(57) ABSTRACT

A time-resolved, fluorescence spectrometer makes use of a RadiaLight® optical switch and no dispersive optical elements (DOE) like gratings. The structure is unique in its compactness and simplicity of operation. In one embodiment, the spectrometer makes use of only one photo-detector and an efficient linear regression algorithm. The structure offers a time resolution, for multiple species measurements, of less than 1 s. The structure can also be used to perform fluorescence correlation spectroscopy and fluorescence cross-correlation spectroscopy.

9 Claims, 20 Drawing Sheets

OTHER PUBLICATIONS

Beechem, J. et al. The Global Analysis of Fluorescence Intensity and Anisotropy Decay Data: Second-Generation Theory and Programs. Topics in Fluorescence Spectrocopy, vol. 2; Principles, edited by Joseph R. Lakowicz. Plenum Press, New York, 1991. pp. 241-305. Eg. 5.14. 45.15; p. 257; pare 4-5; section 5.7.2 (65 pages).

M. Ameloot, J.M. Beechem, L. Brand; "Simultaneous Analysis of Multiple Fluorescence Decay Curves By Laplace Transforms", Biophysical Chemistry 23, 155171 (1986).

J.N. Demas, B.A. DeGraff; "On the Design of Luminescence Based Temperature Sensors", SPIE Proceedings vol. 1796, 71-75 (1992).

L. Sacksteder, M. Lee, J.N. Demas, B.A. DeGraff; "Long-Lived, Highly Luminescent Rhenium(I) Complexes as Molecular Probes: Intra- and Intermolecular Excited-State Interactions", J. Am. Chem. Soc. 115, 8230-8238 (1993).

U.S. Appl. No. 11/452,129, filed Jun. 12, 2006, Claps et al.

Lug G. Frechette, Stuart A. Jacobson, Kenneth S. Breuer, Fredric f. Ehrich, Reza Ghodssi, Ravi Khanna, Chee Wei Wong, Xin Zhang, Martin A. Schmidt and Alan H. Epstein: Demonstration of a macro fabricated high-speed turbine supported on gas bearing: Solid-State Sensor and Actuator Workshop, Hilton Head Is., CS, Jun. 4-8, 2000).

H.M. Rowe, W. Xu, J.N. Demas, B.A. DeGraff; "Metal Ion Sensors Based on a Luminescent Ruthenium (II) Complex: The Role of Polymer Support in Sensing Properties", Appl. Spectrosc. 56(2) 167-173 (2002).

Elmar Thews, Margarita Gerken, Reiner Eckert, Johannes Zapfel, Carsten Tietz and Jorg Wrachtrup: "Cross Talk Free Fluorescence Cross Colleration Spectroscopy in Live Cells" Biophysical Journal, vol. 89, Sep. 2005.

* cited by examiner

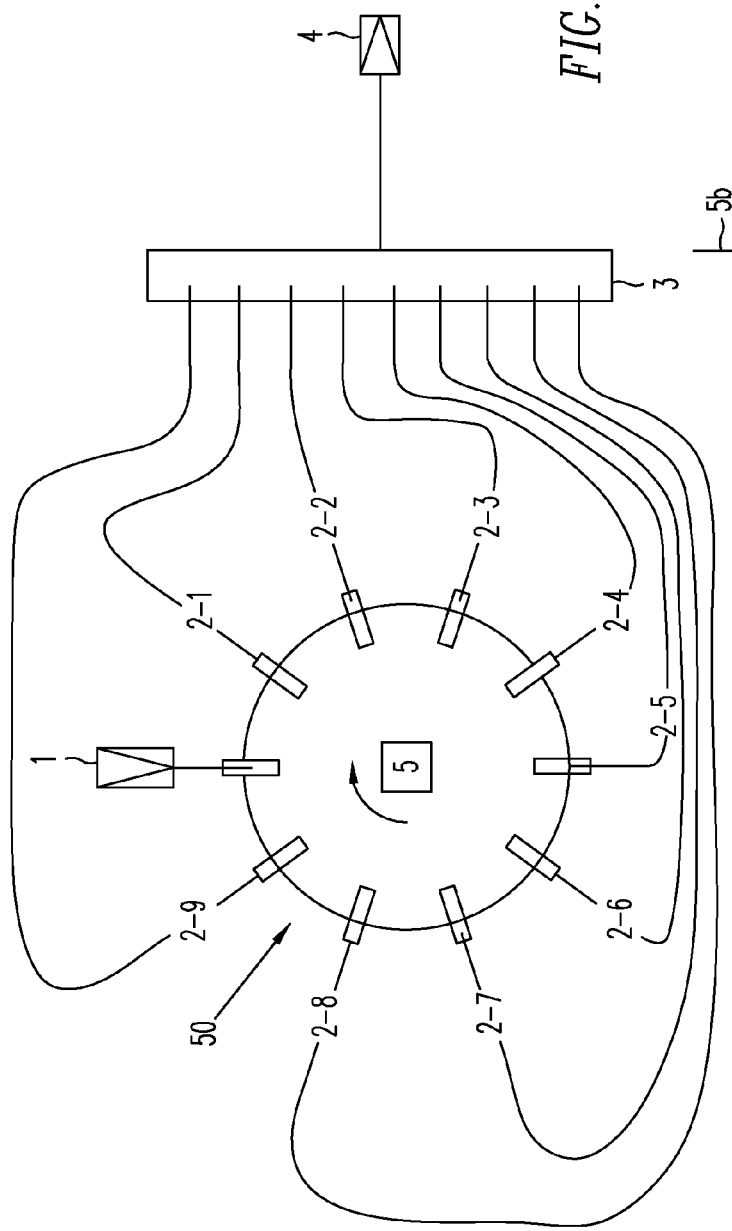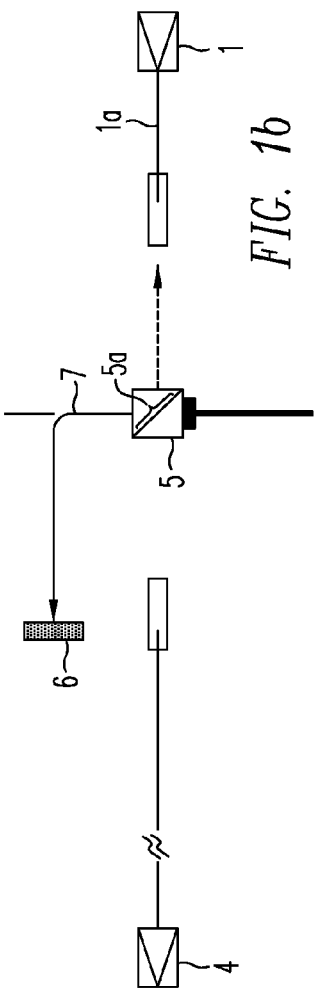

TIME-RESOLVED FLUORESCENCE SPECTROMETER FOR MULTIPLE-SPECIES ANALYSIS

FIELD OF THE INVENTION

This invention relates to a time-resolved fluorescence spectrometer that is capable of measuring samples with multiple components simultaneously. The instrument is environmentally rugged, has low cost, and can be used in field applications where other fluorescence techniques could not be implemented.

BACKGROUND OF THE INVENTION

Fluorescence spectroscopy is a widely used technique in the Biological sciences. In fluorescence spectroscopy, light at a specific frequency is absorbed by a given molecule or fluorescent entity (also called fluorophore), exciting its electronic state. The fluorescent entity then emits light at a slightly different frequency, as the fluorophore returns to the original ground state. Fluorescence spectroscopy is analogous to Raman spectroscopy in that a pump light excitation induces the emission of Stokes light, shifted to a lower frequency relative to the pump light. However, fluorescence requires the absorption of the pump light of a specific frequency, the frequency depending on the electronic structure of the fluorescent entity. Also, contrary to Raman scattering, typical Stokes shifts for fluorescence phenomena are a few 10's of nm apart from the pump light, which complicates the cross-talk between the pump light and the Stokes signals at the detection level. Furthermore, as opposed to Raman scattering, which is essentially instantaneous, fluorescence emission takes place across a wide range of lifetimes, within a few ns or up to a few ms, depending on the fluorophore.

Fluorescence spectroscopy methods can be divided into two broad areas: secondary fluorescence and intrinsic fluorescence. Secondary fluorescence uses certain predetermined fluorophores as marker substances (chemical compounds or quantum dots, for example). These fluorophore molecules attach themselves to a specific protein, enzyme, or DNA string, called a target substance; by doing so, their fluorescent capacity is either enhanced or suppressed. The detection of fluorescence activity or its relative change therefore enables the measurement and identification of the desired target. In the past decades, great effort has been devoted to the development of fluorescent molecules that act as chemical markers for a wide variety of target substances relevant in the biochemical, pharmaceutical, and medical arenas. Intrinsic fluorescence uses the fluorescence emission of the target molecules themselves, which limits its application to strongly emitting targets.

Time-resolved fluorescence (TRF) is a technique that has all the advantages of fluorescence spectroscopy, with the added benefit of being intrinsically related to the target substance, eliminating concerns about absolute intensity measurements. As a result, interference from different chromophores, diverse scattering mechanisms from the sample and effects like photo-bleaching become transparent to the technique. This makes TRF a method of choice for developing fluorescence-based sensors for biological and biochemical studies. Typically in these applications, the fluorescent molecules used are large organic complexes or quantum dots such that fluorescent lifetimes are quite short, less than 10 ns. Any application of TRF in this regime implies the use of pulsed lasers and high-end detection techniques: ultra fast photo detectors or high frequency modulators and RF filters.

In general, fluorescence spectroscopy techniques are mostly limited to laboratory environments due to the following reasons:

1) Short lifetime measurement techniques require the use of expensive and delicate equipment: pulsed pump lasers and state-of-the-art synchronized photo-detection schemes.

2) Fluorescence spectroscopy instrumentation is bulky.

3) Conventional fluorescence techniques require the use of high performance optical filters. This adds on to the price of the instrument, its complexity, and reduces the signal collection efficiency. It also increases the cross-talk between pump and Stokes signals, and between the Stokes signals from different fluorophores.

4) Due to the extra complexity and cross-talk added by the optical filtering procedures, only small number of target substances can be analyzed simultaneously (3 or 4 at a time).

5) In fluorescence lifetime measurements, fluorophore concentration values are normally disregarded, as the measurement technique is only involved with relative changes of the signal in time. Also, the analytical complexity of deriving both lifetime and concentration values increases rapidly with the number of targets being analyzed. As a result, current lifetime fluorescent techniques are limited to fixed concentration measurements for a few target substances (2, 3 or 4).

6) Due to the close spectral proximity between the pump and Stokes signals in fluorescence spectra, and between Stokes signals from different fluorophores, high-performance optical filtering techniques are required. This increases cost and complexity of typical fluorescence devices.

In view of the above, there is a need for a TRF device that can be implemented in field applications under harsh environmental conditions. These applications usually require measurement of multiple targets (10 to 25) simultaneously. A complete measurement and sample assessment needs to be performed in a time frame of 1 s or less. Such a device would not only find new applications but also enhance current technologies like DNA sequencing and fluorescence imaging microscopy.

SUMMARY OF THE INVENTION

In accordance with the present invention a device such as a RadiaLight® switch is used for the implementation of a TRF instrument that has the quality of being compact, rugged and fast (with measurement times of less than 1 s). The instrument can perform single and multiple species (10 to 25) analysis, with the capability of measuring fluorescence intensity and/or lifetime decay.

An embodiment of the system uses the RadiaLight® switch as a time-division multiplexing device that delivers a pulsed fluorescent pump light sequentially into one or more samples. At the same time, the RadiaLight® device collects the fluorescence produced by each sample in a synchronized sequence of pulses, thus providing a precise temporal profile of the fluorescence signal induced by the pump pulse. By using long lifetime-decay fluorophores, the device can perform TRF spectroscopy within the period of one or a few cycles of the RadiaLight® switch. To achieve this, transition metal complexes (TMCs, also known as Metal-Ligand-Complexes, MLC's) such as $[Ru(Ph_2phen)_3]Cl_2$, can be used as the fluorophores. These fluorophores have the property of long excited state lifetimes (0.1->5 µs), high quantum yields (0.04-0.5), and strong ultraviolet-visible (UV-visible) absorption. (see J. N. Demas, B. A. DeGraff; "On the Design of Luminescence Based Temperature Sensors", SPIE Proceedings Vol. 1796, 71-75 (1992); H. M. Rowe, W. Xu, J. N.

Demas, B. A. DeGraff; "Metal Ion Sensors Based on a Luminescent Ruthenium (II) Complex: The Role of Polymer Support in Sensing Properties", Appl. Spectrosc. 56(2) 167-173 (2002); L. Sacksteder, M. Lee, J. N. Demas, B. A. DeGraff; "Long-Lived, Highly Luminescent Rhenium(I) Complexes as Molecular Probes: Intra- and Intermolecular Excited-State Interactions", J. Am. Chem. Soc. 115, 8230-8238 (1993); and T. Harri Takalo, K. Veli-Matti. Mukkala; "Luminescent Lanthanide Chelates", U.S. Pat. No. 5,571,897, Nov. 5 (1996)). Luminescent lifetimes as long as 100's of µs have been measured for Lanthanide complexes. (See U.S. Pat. No. 5,571, 897). The lifetimes of these TMCs fall precisely within the range of time-resolution capabilities of the RadiaLight® switch. In this embodiment, the device can perform TRF of a sample with a plurality of components, each of them associated with a fluorophore that has a distinct decay time that lies within the time range detectable by the device.

Another embodiment of the invention combines the time-division multiplexing capability of the device with the ability to use a plurality of optical band-pass filters for each optical channel. This embodiment enhances the multiplicity of components that the invention can analyze simultaneously, by using fluorophores that have different lifetimes and different emission spectra.

Another embodiment of the invention makes use of device architecture analogous to that disclosed in co-pending patent application Ser. No. 11/452,129, filed Jun. 12, 2006, assigned to Neptec Optical Solutions, Inc., the assignee of this application. Application Ser. No. 11/452,129 is hereby incorporated herein by reference in its entirety. In this embodiment, the fluorescence pump light is not pulsed by the time-division optical multiplexer device, but illuminates the sample continuously. The fluorescence radiation is collected and passed through the time-division optical multiplexer, which directs the radiation into a sensitive photodetector as a sequence of pulses, each of which has been spectrally filtered in order to separate the Stokes signal from different fluorophores. In this embodiment, the fluorescent decay lifetime of the fluorophores has to be faster than the intra-channel period of measurement, also known as dwell time of the device ($\Delta T$). In this embodiment, the present invention can be used to perform fluorescence correlation spectroscopy (FCS) and fluorescence cross-correlation spectroscopy (FCCS).

In summary, in accordance with the present invention a device is provided that performs time-resolved Fluorescence spectroscopy enabling multiple-component monitoring with environmental ruggedness and enhanced processing speed. The device has the following unique properties:

1) Processes and analyzes multiple component samples with a time resolution of 1 ms to 100 ms.

2) The ability to use an ultra-sensitive photo-detector to enhance the sensitivity at high speed.

3) Provides a simple time-calibration of the fluorescence signal, therefore improving the accuracy of data collection at a reduced cost.

4) Can quantitatively determine a mixture composed of multiple components (20-25+components), simultaneously.

5) Is field-deployable, suitable to be used in moving vehicles and aircraft, and hostile physical environments, with no degraded performance.

6) Can operate in any given orientation relative to the ground, with no need for readjustments due to gravity.

7) Represents a factor of ten (10) manufacturing cost reduction, relative to similar instruments, due to the reduced number of parts used and simplicity of construction.

8) Provides a wide bandwidth of detection, from 300 nm to 1.0 µm, or 900 nm to 1.5 µm, depending on the photodetector material chosen.

9) Eliminates the use of gratings, prisms, and other dispersive elements that are lossy, expensive, and extremely sensitive to alignment.

10) In one embodiment of the invention, the use of optical filters is completely eliminated in the device.

11) Uses a single photosensitive element, replacing the need for photo-detector arrays and CCD cameras, and simplifying data collection schemes.

12) Uses a linear regression algorithm for data processing, reducing the number of data points to be handled by an order of magnitude.

13) Uses an algorithm that incorporates an auxiliary time-dependent function, to measure fluorescent target concentration and fluorescence decay lifetime of multiple analytes, simultaneously.

14) Uses an algorithm that incorporates a discrete Laplace Transform technique, and a step-speed scan technique, to measure fluorescent target concentration and fluorescence decay lifetime of multiple analytes, simultaneously.

15) Uses an algorithm that incorporates a discrete Laplace Transform technique, and a continuous-speed scan technique, to measure fluorescent target concentration and fluorescence decay lifetime of multiple analytes, simultaneously.

16) Allows for a method to perform real-time, non-invasive temperature measurements of samples in-vivo or for other applications, based on Fluorescence-lifetime spectroscopy.

17) Allows for a method to determine multi-component concentrations in a given sample, using Fluorescence-lifetime spectroscopy and linear regression techniques. In this methodology, the sample can be a solid, a powder, a liquid, or a gas.

Potential applications include the development of in-vivo blood gas sensors, based on Fluorescence life-time measurement techniques: $CO_2$, $O_2$, pH, the development of oxygen sensors for industrial applications such as semiconductor manufacturing and combustion diagnostics, and the development of in-vivo, time-resolved metal ion sensors such as $Cu^{+2}$, $Na^+$, $Ca^+$, which are relevant for physiological diagnostics.

This invention will be more fully understood in view of the following drawings taken together with the following detailed description.

DESCRIPTION OF THE DRAWINGS

FIGS. 1a and 1b show schematically top and side views of one embodiment of the invention, respectively, using a time-resolved optical switch, an optical pump source, and a photo-detecting element.

FIG. 3a shows an embodiment of this invention using a multiplicity of optical filters 3-1 to 3-9 in order to perform lifetime measurements of different fluorophores ($S_1$, $S_2$, $S_3$). The filters are arranged in sequence such that three (3) consecutive channels correspond to the three different substances represented in the FIG. 3a. In FIG. 3a, the sequence of three different filters is repeated three times. Other numbers of channels can be used in this embodiment if desired.

FIG. 12 (b) shows the theoretical time-profile of the fluorescence signal in three different optical channels of the device. The measurement configuration of the device shown in FIGS. 1a and 1b corresponds to the continuous speed scan algorithm Number 4 described herein for fluorescent lifetime and concentration measurements.

DETAILED DESCRIPTION OF THE INVENTION

Figure 2:
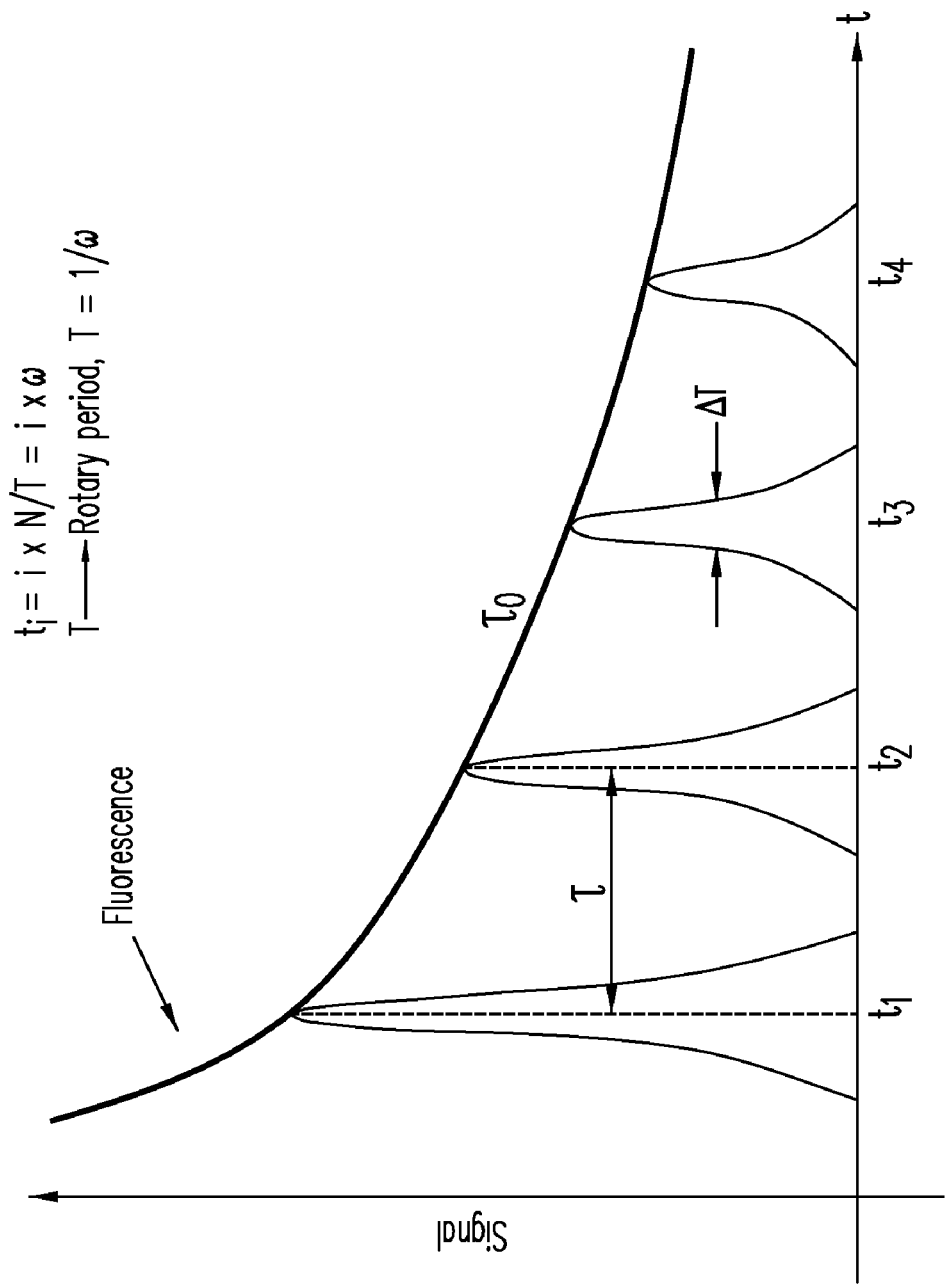
FIG. 2 shows the theoretical time profile of a typical fluorescence signal, as measured by the photo-detector from FIGS. 1a and 1b.

The following detailed description is meant to be illustrative only and not limiting. Other embodiments of this invention will be obvious to those skilled in the art in view of this description.

In accordance with this invention a time-resolved, fluorescence spectrometry device architecture is provided that combines a high-speed time-division optical sampling engine with a unique data processing algorithm, discrete Principal Component Analysis (dPCA), in order to produce time-resolved, accurate fluorescence measurements with low signal levels. A variety of specific embodiments can be provided to implement the invention. The invention significantly decreases the sample processing time, while increasing the number of material samples that can be processed at one time. This invention also improves the environmental ruggedness of the device while significantly reducing the implementation cost.

Referring to FIGS. 1a and 1b, one embodiment of this invention employs a rotary switch such as disclosed in co-pending patent application Ser. No. 11/185,137 filed Jul. 20, 2005 (RadiaLight®) based on provisional application No. 60/589,454 filed Jul. 20, 2004, both assigned to Neptec Optical Solutions, Inc., the assignee of this application. These two applications are hereby incorporated by reference in their entirety. This rotary switch essentially acts as a time-division multiplexing device. In the structure of FIGS. 1a and 1b, (which corresponds to the best mode of the invention), light from a pump laser 1 (or other source such as a SLED (a "super-luminescent light emitting diode") or a gas emission lamp using halogen gases or mercury or equivalent) is transmitted along a path 1a to a rotating prism 5 containing a reflecting surface 5a which reflects the light from laser 1 along a waveguide 7 to illuminate a material sample 6 to be interrogated. Sample 6 contains a fluorophore which, in response to incident light from laser 1, emits fluorescent light back along waveguide 7 to rotating prism 5. Fluorescent light emitted from the sample (called information light or "Stokes radiation") contains specific information about the chemical and physical make up of the material being interrogated. Hereafter, in this written description, the term "Stokes radiation" will be used to mean the same as "information light", which is fluorescent light emitted from the sample as a result of light from source 1 impinging on sample 6.

In the embodiment of FIGS. 1a and 1b, the optical delivery of the light from the illumination source and the optical collection from sample 6 of the Stokes radiation are performed through the same fiber 7 (sometimes called a "waveguide"). As shown in FIGS. 1a and 1b, the light from source 1 to be incident on sample 6 is transmitted to optical fiber 7, through one of the channels of the RadiaLight® time division multiplexer 50. In this manner, even if the light source 1 is operating in continuous mode (CW), the pump light in the delivery channel 7 has a pulsed time profile because prism 5 is rotating at a selected speed driven by a precision electric motor. This motor can be any of several well known commercially available motors of a type used, for example, in gyroscopes. In one embodiment, this motor can rotate at extremely high speeds such as up to 200,000 RPM or more if required.

Fluorescence is emitted from sample 6 throughout a period of time comparable to the fluorescence lifetime, $\tau_0$. This fluorescent light is carried back from sample 6 into the RadiaLight® device 50 by waveguide 7. Notice that, since there is a time delay, $\tau$, between the pump pulse from laser 1 and the fluorescence signal carried back from sample 6 to rotating prism 5, there is no need to have a filter or a circulator in series with waveguide 7. In most fluorescence spectrometers, as well as in any typical Raman device, this filter is necessary in order to block the pump light from the photo-detector in the instrument. In multiplexing device 50 reflecting prism 5 rotates about axis 5b which is perpendicular to the path 1a along which light from laser 1 is sent to prism 5. Because prism 5 rotates at a selected rotational speed, the fluorescent light from sample 6 which travels back along waveguide 7 to prism 5 is reflected by the mirror 5a in prism 5 to one or more channels 2-i (where i is an integer given by $1 \leq i \leq I$ where I is the maximum number of channels) located about the circumferential perimeter of stationary platform 5c, at a different time than that at which the initial illuminating pulse from pump laser 1 hits the sample 6. Platform 5c holds a plurality of channels 2-i (shown in FIG. 1b as waveguides 2-1 to 2-9) each of which will receive a portion of the fluorescent signal emitted from sample 6 as prism 5 rotates. Of course, the strength of the fluorescent signal emitted from sample 6 will decrease with time. The rate of decrease will depend upon the lifetime of the fluorophore used with sample 6 and can vary from as short as a few nanoseconds to as much as several milliseconds or even seconds.

The RadiaLight® optical switch includes a motor-driven, rotating prism 5 (see patent application Ser. No. 11/185,137 filed Jul. 20, 2005, published Apr. 6, 2006 as U.S. Publication No. 2006/0072873 A1) incorporated by reference above. The mirrored surfaces of prism 5 reflect the light incoming through channel 7 into one of several waveguides or channels 2-1 to 2-9, arranged circularly in a plane perpendicular to the z-axis 5b of rotation and centered about the z-axis of rotation. While nine (9) waveguides 2-1 through 2-9 are shown arranged in a circle in a plane around the rotating prism 5, of course, a smaller or larger number of waveguides can be so arranged if desired. For example, in some embodiments 20 to 100 waveguides will be so arranged around the circumference of the rotating prism 5 within a plane to enable the system to determine at least 20 to 100 characteristics of the sample being analyzed.

In the structure of FIG. 1b, the rotation of the prism 5 sweeps the Stokes radiation beam across the inputs of the several waveguides 2-1 to 2-9, creating a discrete time profile of the continuous Stokes emission beam. Thereby, each waveguide receives a time slice of the original optical information signal (i.e. the Stokes emission). Each waveguide 2-i (where i is an integer varying from 1 to N when N waveguides are placed around the perimeter of platform 5c in the plane perpendicular to the z-axis 5b of rotation) is associated with a specific time slot, $t_i$, of the Stokes emission. The Stokes emission passing through waveguides 2-1 to 2-9 is then directed through multiplexer 3 of well known design to a single optical detector 4. The signal from optical detector 4 is sent into electronic analytical equipment, such as a computer, for processing. The electronic analytical equipment, including the photodetector 4, can be of the kind and form such as disclosed in co-pending patent application Ser. No. 11/452,129, filed Jun. 12, 2006, assigned to Neptec Optical Solutions, Inc., the assignee of this application and incorporated by reference in its entirety above.

The multiplexer 3 (which might be based on single mode fiber, multi-mode fiber, or a photonic crystal fiber (PCF) depending on the desired numerical aperture, bandwidth and transmission loss of the device) will pass the signal being transmitted on the corresponding fiber 2-i when fluorescence light reflected from the rotating prism 5 impacts the corresponding waveguide, 2-i. The speed of rotation of prism 5, designated by the symbol, $\omega$, determines the frequency with which the signal processing unit (which might, for example, include a digital signal processor, certain recognition algorithms and a computer for carrying out the processing) receives the signals from each of the waveguides 2-1 through 2-9 on FIG. 1.

FIG. 2 shows the theoretical time-profile of the fluorescence signal in the instrument, as measured by the photodetector. The thick, continuous line shows the natural decay of fluorescence emission, with lifetime $\tau_0$. The emission is transmitted in discrete time slots by adjacent waveguides 2-1 (corresponding to time slot $t_1$ in FIG. 2) through 2-9 in FIG. 1a of the RadiaLight® switch 50. Each waveguide 2-i transmits a fluorescent signal occurring at a time $t_i$, where the index i goes from 1 to N, the number of optical channels or waveguides 2-i in the RadiaLight® switch 50. The time elapsed between each Stokes pulse, $\tau$, depends on the speed, $\omega$, of the time-division multiplexer. The pulse-width of the time slots is the same for each Stokes pulse, as long as the rotational speed, $\omega$, is kept constant. This pulse-width will be referred to as dwell time ($\Delta T$) and depends on the speed, $\omega$, and the geometry of the switch. By increasing the speed of rotation of the prism 5, the time resolution, $\tau$, is reduced accordingly, at the cost of reducing the measurement time, $\Delta T$. In this manner, fluorophores with faster decay times can be analyzed with the instrument.

Figure 3A:
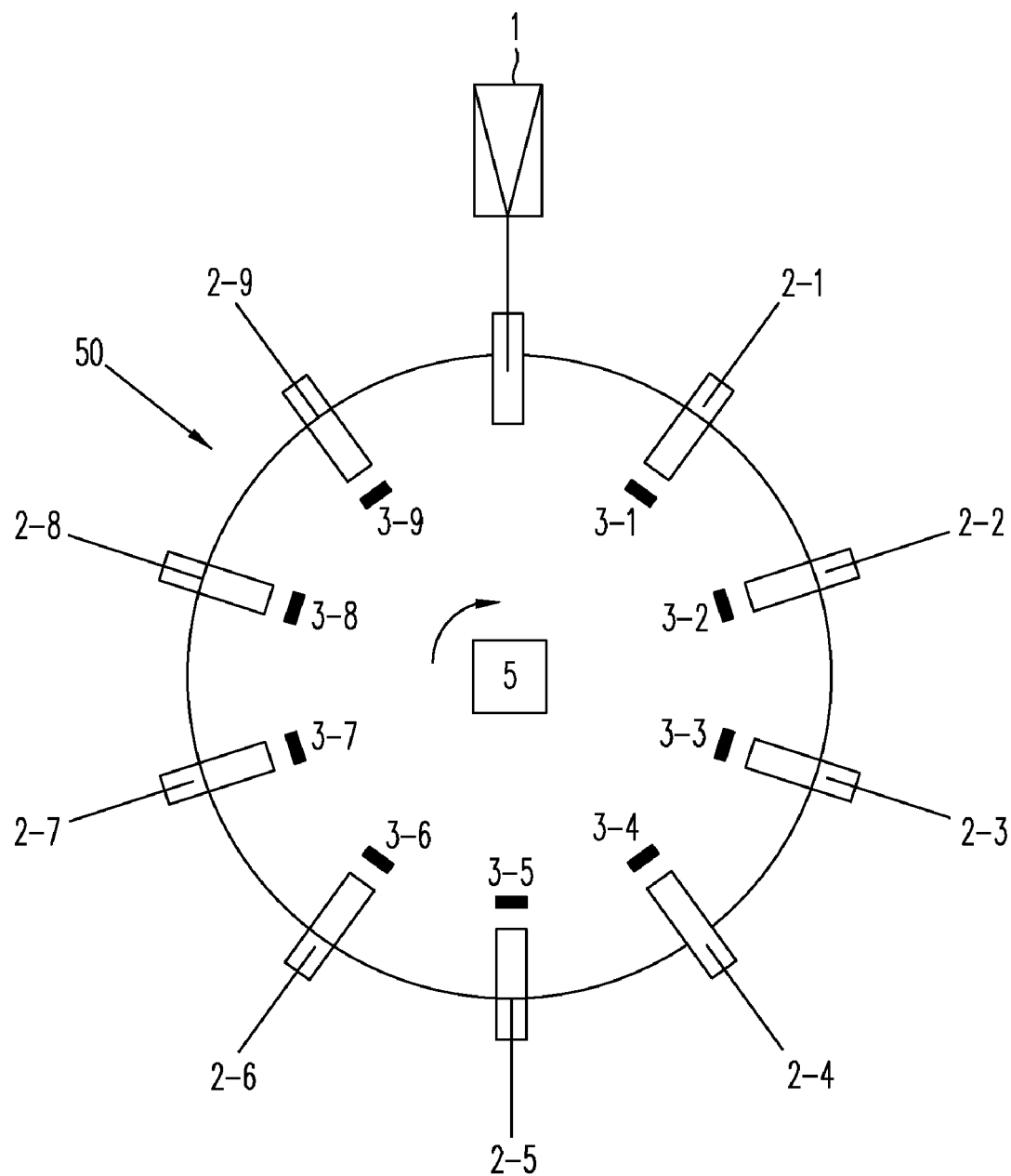
Figure 3B:
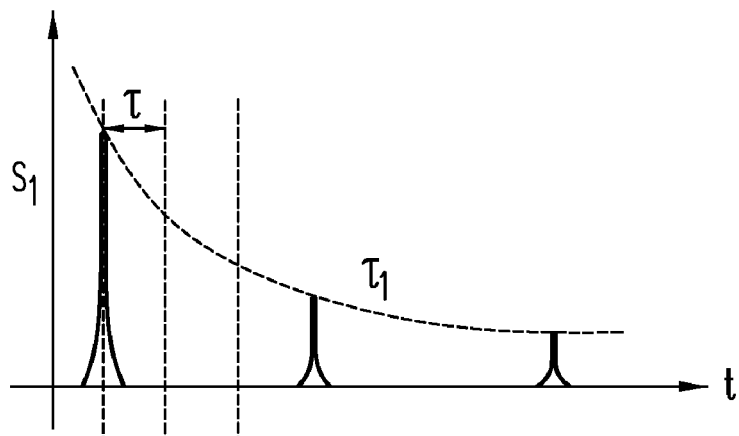
FIGS. 3b, 3c, and 3d show the waveforms as detected by the photodetector or photodetectors attached to the channels 2-1 to 2-9.
Figure 3C:
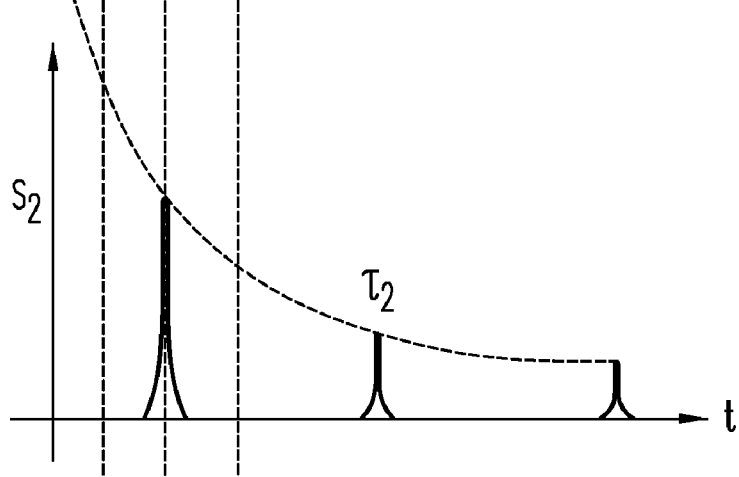
Figure 3D:
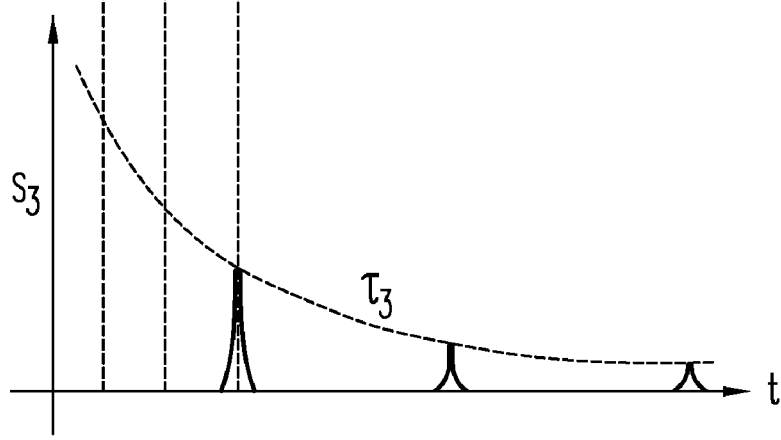

In another embodiment of the invention, illustrated in FIG. 3a, a plurality of optical filters 3-1 through 3-9 is used in the RadiaLight® body 5c in order to distinguish between the Stokes emissions of a plurality of fluorophores placed on the sample 6. FIGS. 3b, 3c and 3d show, respectively, the decay times of three different components $S_1$, $S_2$, and $S_3$ of the sample 6 being analyzed. Notice that reflected light from component $S_1$ is passed by filters 3-1, 3-4 and 3-7 to channels 2-1, 2-4 and 2-7, respectively. Reflected light from component $S_2$ is passed by filters 3-3, 3-6, and 3-9 to channels 2-3, 2-6 and 2-9, respectively, while reflected light from component $S_3$ is passed by filters 3-2, 3-5, and 3-8 to channels 2-2, 2-5, and 2-8, respectively. The time shifts of the reflected fluorescent light pulses shown in FIGS. 3b, 3c, and 3d reflect the times for prism 5 to rotate so as to direct the reflected light to the appropriate channels 2-1 to 2-9 in sequence. Filters 3-1 through 3-9 allow only the light from the desired fluorophore to pass into the appropriate channel 2-1 through 2-9.

Figure 4A:
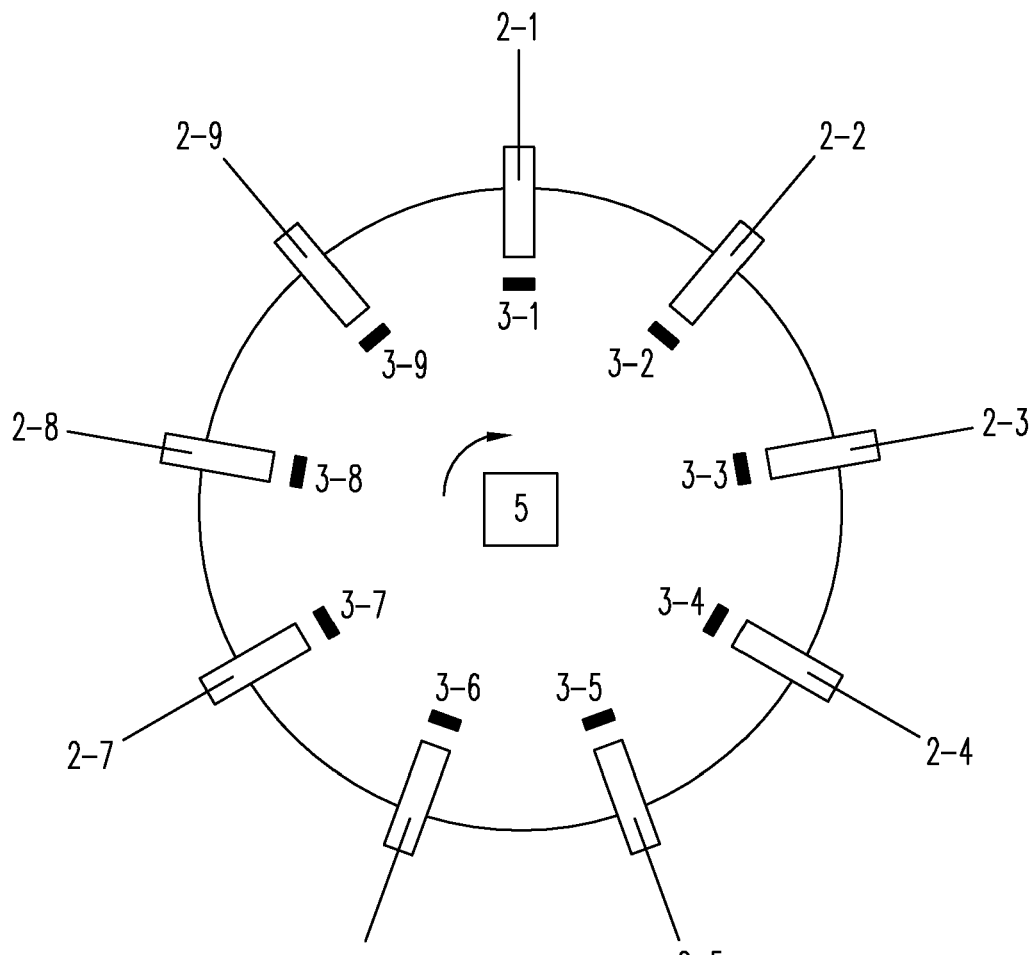
FIGS. 4a and 4b show an embodiment of this invention using a multiplicity of optical filters 3-1 to 3-9 to perform fluorescence correlation spectroscopy (FCS) and fluorescence cross-correlation spectroscopy (FCCS). A blocking filter, 9, is introduced to prevent the pump light reflected off of the sample from going into the detecting device.
Figure 4B:
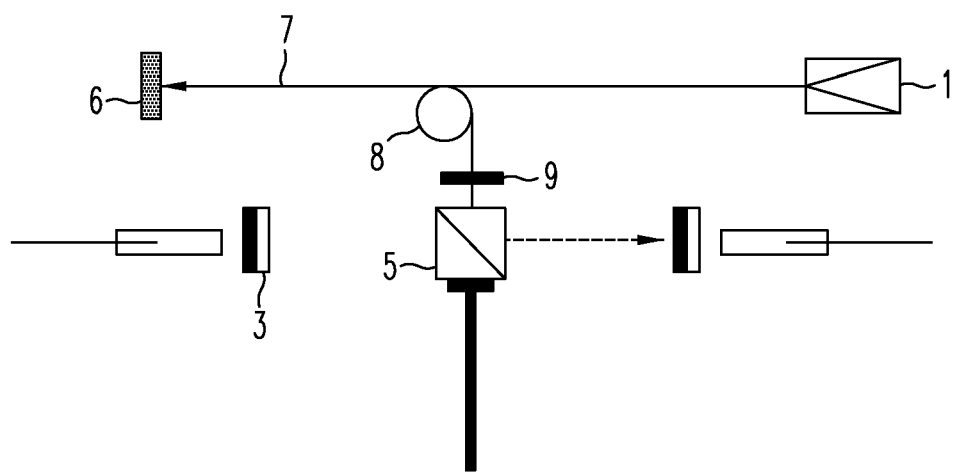

Another embodiment of the invention is illustrated in FIGS. 4a and 4b. Here, a plurality of optical filters 3-1 through 3-9 is also used to distinguish between the Stokes emissions of a plurality of fluorophores. In this case, the fluorescence signals are produced and collected at different time intervals; the pump optical signal from laser 1 is continuous, and the decay lifetime of the fluorophores can be as short as a few ns, but no longer than the $\Delta T$ (see FIG. 2 for a definition of $\Delta T$) of the RadiaLight® device 50 at the operational speed. The pump optical signal from laser 1 is transmitted along waveguide 7 to sample 6 and the reflected radiation from sample 6 is passed back along waveguide 7 to routing element 8 and then through an additional filter 9 which blocks the light from laser 1. This configuration enables the use of correlation techniques between different fluorophores (FCCS), or auto-correlation techniques for each target (FCS). Also note that for this configuration additional filter 9 is needed before or after the routing element 8 (shown in FIG. 4a as after the routing element 8), so as to block all light that contains the frequency of the pump light from going into the RadiaLight® switch device 50 and from there into the waveguide channels 2-1 through 2-9.

The algorithms used by the present invention to measure the fluorescence signal from a sample that is composed of a plurality of fluorophores that have different emission decay lifetimes, $\tau_1$, will be disclosed in the following. Four different algorithms will be disclosed. All the algorithms disclosed herein are devised so that they can operate with the time-resolved fluorescence spectrometer disclosed in FIGS. 1a and 1b. However, any person skilled in the art will recognize that the field of application of the algorithms disclosed herein can be broader than the uses described herein. In particular, the following algorithms 1 through 4 can be implemented together with any time-resolved instrumentation in order to perform multiple species evaluation of exponentially decaying processes. The first algorithm belongs to a wider set of techniques that in accordance with this invention will be called discrete Principal Component Analysis (dPCA). The first algorithm involves the use of dPCA techniques to evaluate the concentrations of multiple analytes simultaneously in a given sample, each analyte having determined and fixed fluorescent lifetime decay, or attached to a fluorophore that has determined and fixed lifetime decay. The other three algorithms are concerned with the evaluation of both the concentrations and the lifetimes of multiple analytes simultaneously, in a given sample. The second of these algorithms makes use of a dPCA technique supplemented with an auxiliary function (see equation 8). The last two algorithms do not belong to the set of dPCA algorithms, but to a set that will be called "discrete Laplace Transform" techniques. One of these two algorithms makes use of a discrete speed scan of the time-resolved spectrometer, and the other uses a continuous speed scan of the time-resolved spectrometer and integration in discrete time-segments of the signal.

Algorithm No. 1.

Notwithstanding the spectral composition of the fluorescence emission coming from the different analytes in the sample, the intensity of fluorescence radiation produced by a number of fluorescent analytes (say, K), as a function of time, is simply given as the incoherent addition of each individual analyte, $$I_F(t) = \sum_i^K \alpha_i \eta_i \chi_i \cdot e^{-t/\tau_i} \tag{1}$$

where, $\chi_i$, is the concentration of the i-th substance, $\alpha_i$, its absorbance, $\eta_i$, its fluorescence quantum efficiency and, $\tau_i$, its fluorescence lifetime. To arrive at Eq (1), the limit of small absorbance for the analytes is assumed. Since $\{\alpha_i\}$ and $\{\alpha_i\eta_i\}$ are fixed quantities, we can recombine the three factors in the coefficients of Eq. (1) as a single set of unknowns, $\{\zeta_i\}=\{\alpha_i\eta_i\chi_i\}$. An analyte can be an atom, a molecule or a compound. An analyte is sometimes called a component. Typically, a sample of material being analyzed will contain a plurality of components or analytes.

In one of the embodiments of the instrument, it will be assumed that the lifetimes, $\{\tau_i\}$, of the analytes are known values which remain constant during the course of the measurement and are only slightly affected by environmental conditions (such as pH, Temperature, viscosity, humidity pressure). In this case, the analyte concentration, $\{\chi_i\}$ is being measured, and the time-resolution is understood as the ability of the RadiaLight® fluorometer to determine $\{\chi_i\}$ within a time window equal to the roundtrip time of the device. The linearity of Eq. (1), with respect to analyte concentrations, $\{\chi_i\}$, allows for the use of linear regression techniques in de-convolving the time-domain signal at the photodetector level, when a sample composed of a plurality of fluorescent substances is being interrogated. By defining the elements of an N×K matrix, $\sigma$, as $$\sigma_{ij} = \frac{\alpha_j \eta_j}{N \cdot \Delta T} \int_0^T e^{-t/\tau_j} \cdot e^{-(t-t_i)^2/\Delta T^2} dt \tag{2}$$

$i = 1 \ldots N \rightarrow$ number of optical channels;

$j = 1 \ldots k \rightarrow$ number of analytes.

Furthermore, defining a vector, A $(a_1 \ldots a_N)$, where $a_i$ is the integrated optical power received by the photodetector after polling the i-th channel, divided by the dwell time, $\Delta T$ (see FIG. 2), it follows, then $$A = \sigma \cdot \chi \tag{3}$$

Once the photodetector measurement is expressed in a linear operation as shown in Eq. (3), the algebra of regression techniques can be applied directly in a manner such as disclosed in co-pending patent application Ser. No. 11/452,129, filed Jun. 12, 2006, assigned to Neptec Optical Solutions. A new matrix, Z, is defined:

$$Z = \sigma^t \cdot \sigma \tag{4}$$

Z is a square, symmetric matrix, and therefore it can be diagonalized and inverted by a unitary matrix, Q, as in:

$$Z = Q^t \cdot \Lambda \cdot Q \tag{5}$$

where, $\Lambda$, is a diagonal matrix containing the eigenvalues of Z. From Eqs. (3), (4) and (5), a solution can be found for $\chi$ as $$\chi = Q \cdot \Lambda^{-1} \cdot Q^t \cdot \sigma^t \cdot A. \tag{6}$$

Figure 5A:
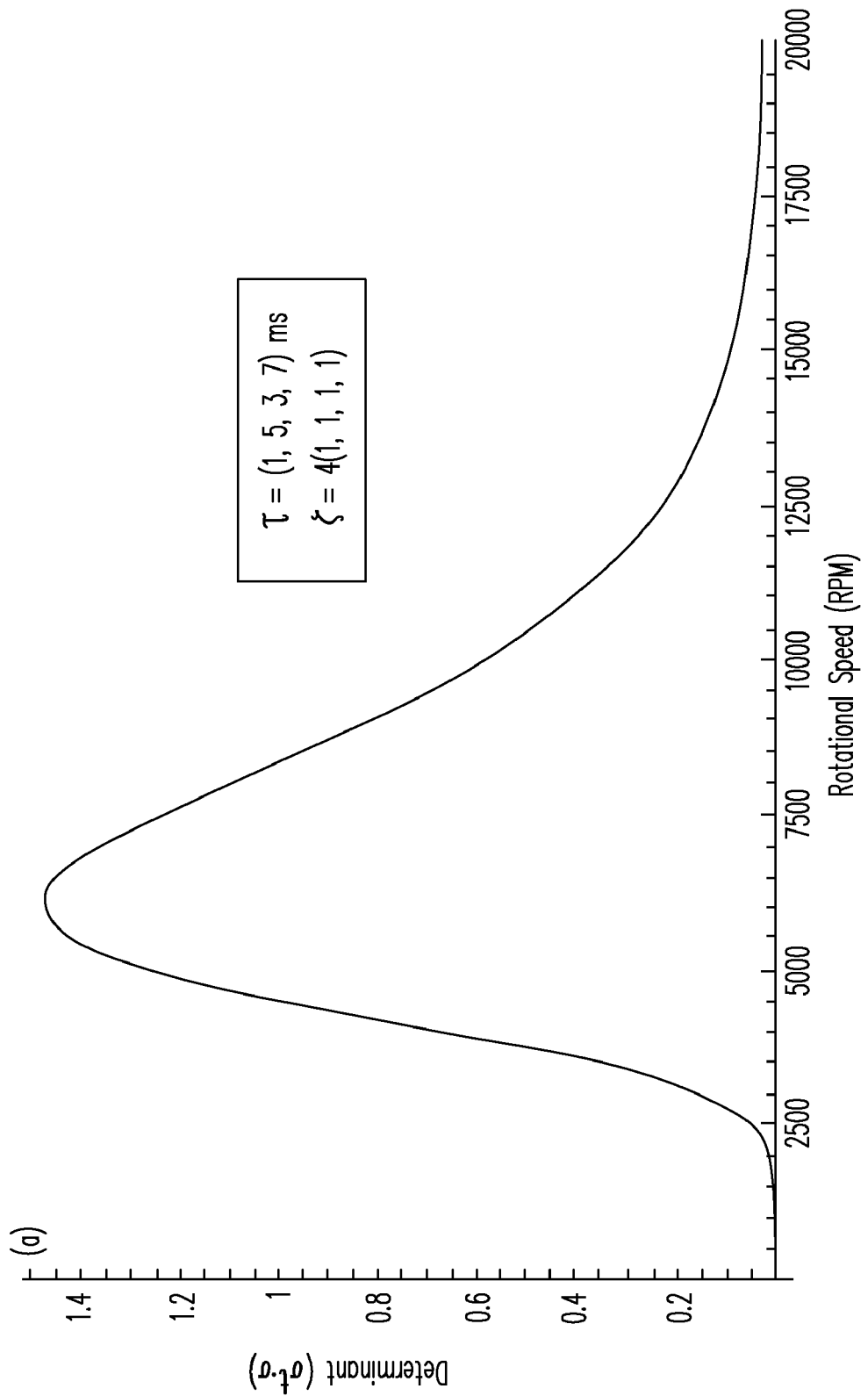
FIGS. 5a and 5b show a determinant, γ, of the matrix, $\sigma^T \cdot \sigma$, defined in Eq. (2), as a function of rotational speed. A sample containing four different fluorophores with equal concentrations is illustrated. The fluorescence spectrometer is operated at the speed that maximizes the determinant. (b) The shorter the lifetime of the analytes, the higher the operational speed of the device needs to be, in order to maximize, γ.
Figure 5B:
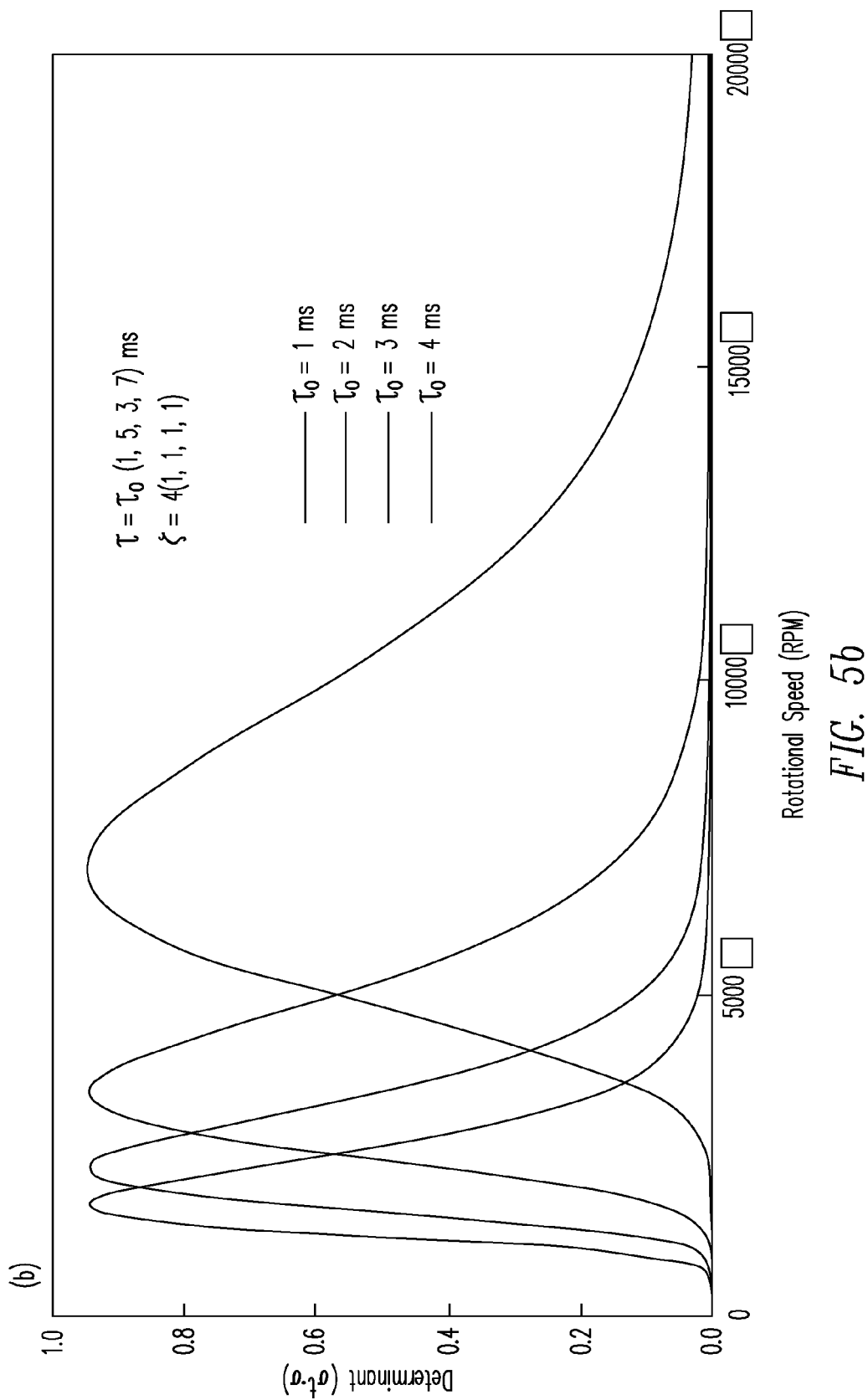

The heart of the device performance lies then in the matrix Z given in Eq. (4). In order for the matrix inversion to allow for minimal error, and for the algorithm to take the least number of operations, the value of, $\gamma = \text{Det}(Z)$, has to be maximized. FIG. 5a shows a plot of $\gamma$ as a function of $\omega$ for a given set of $\{\tau_i\}$ and $\{\alpha_i, \eta_i\}$ of a hypothetical sample. The curve has a clear maximum, and a fairly broad range of values of $\omega$ for which $\gamma$ maintains a sizeable value (FWHM). The operational speed of the device, $\omega_{op}$, will be defined as that which maximizes the curve of FIG. 5a for a given set of $\{\alpha_i, \eta_i\}$. FIG. 5b shows a set of different curves $\gamma$, given samples with a different range of lifetimes $\{\tau_i\}$. Note that the maximum value of $\gamma$ remains the same as the set of values $\{\tau_i\}$ changes substantially. This is convenient since it largely relaxes the computational requirements while the instrument performance is maintained uniform across a large range of lifetime values.

Another indicator of device performance is the variance introduced in the concentration measurement due to the linear regression applied. This information is contained in the rows of the matrix: $Z^{-1} \cdot \sigma^t$. The variance $v$ is defined as $$v = \text{Max}\left[\sum_i (Z^{-1} \cdot \sigma)_{ij}\right]. \tag{7}$$

Figure 6:
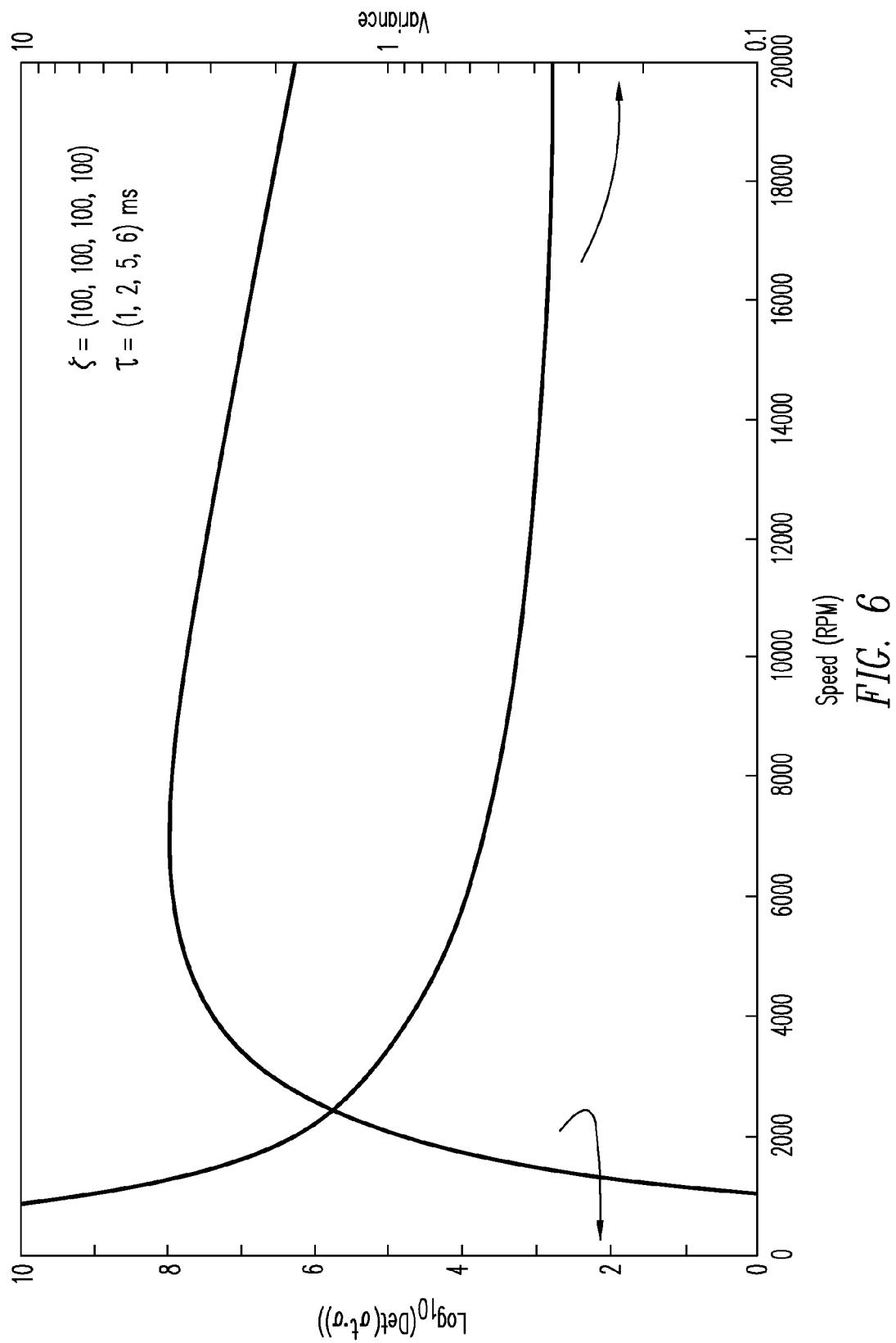
FIG. 6 shows for the set of $\{\tau_i\}$ and $\{\zeta_i\}$ shown, that the value of ω which maximizes γ (Y-axis on the left) also produces a Variance, ν (Y-axis on the right), well below 1, as desired.

FIG. 6 shows the relation between $\gamma$ and $v$ as functions of $\omega$ using the definition of Eq. (7). It is seen that for the range of values that maximize $\gamma$, the values of $v$ are well below 1. This means that the operation of the device is limited only by the photodetector noise and signal statistics rather than by cross-correlation of data in the multi-species analysis.

Algorithm No. 2.

Figure 7:
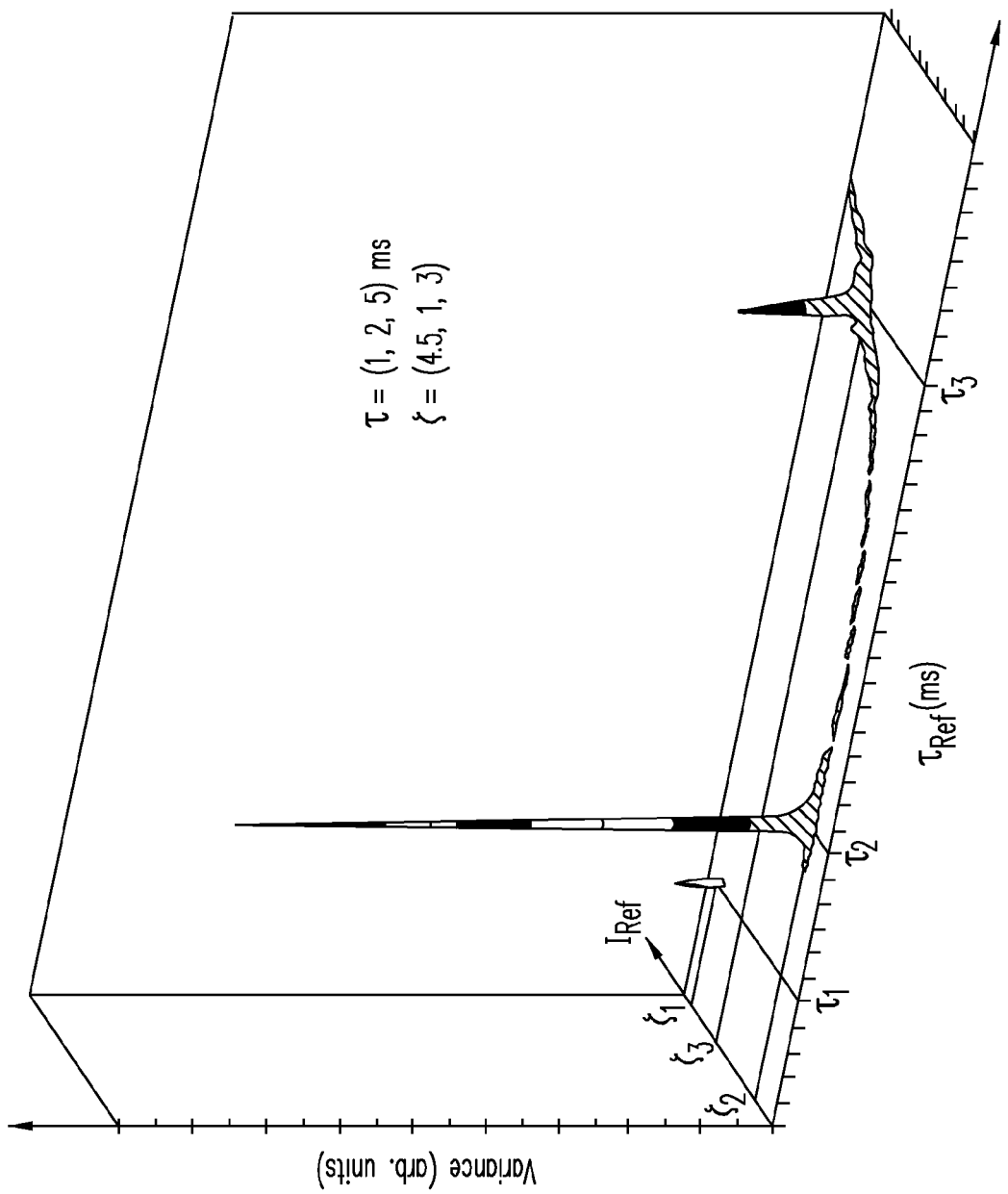
FIG. 7 shows a plot of the variance (Eq. 7) of the signal in the device of FIGS. 1a and 1b as a function of the reference lifetime $\tau_R$, and reference amplitude $I_R$ described in (Eq. 8). A smoothening residual has been added by hand, to avoid the poles of the function. In practice, the inherent dark signals at the photodetector level will prevent the system from being indeterminate and act as a smoothening function. The net result is a surface that shows clear spikes at values of $\tau_R$ and $I_R$ that match the values of the sets: $\{\tau_i\}$ and $\{\zeta_i\}$. The RadiaLight® device simulated has 25 channels (1 mm diameter collimators), and a rotational speed ω=7100 (RPM). At this speed, the sensitivity is maximal for the lifetime range considered. (see FIG. 6)

Using the definition of the variance given in Eq. (7), a further development can be introduced, as described in the following. A reference function $F_R$ can be defined as, $$F_R(t) = I_F(t) + I_{ref} e^{-t/\tau_{ref}}. \tag{8}$$

where $I_F$ is given by Eq. (1), $\tau_{ref}$ is a reference lifetime, and $I_{ref}$ is a reference amplitude. With the function $F_R$ a matrix, $\sigma(I_{ref}, \tau_{ref})$, is built and the variance $v(I_{ref}, \tau_{ref})$, is calculated following Eq. (7). FIG. 7 shows the surface $v(I_{ref}, \tau_{ref})$ for $\tau_{ref}$ ranging from 0 to Max $\{\tau_i\}$, and $I_{Ref}$ ranging from 0 to Max $\{\zeta_i\}$. It is shown that $v(I_{ref}, \tau_{ref})$ has distinct poles at the points, $\{\tau_i, \zeta_i\}$. An operation that produces a function as described in Eq. (8) can be carried out electronically, at the level of the amplifier circuit, or optically, by use of a reference signal of some sort.

Algorithm No. 3.

Figure 8:
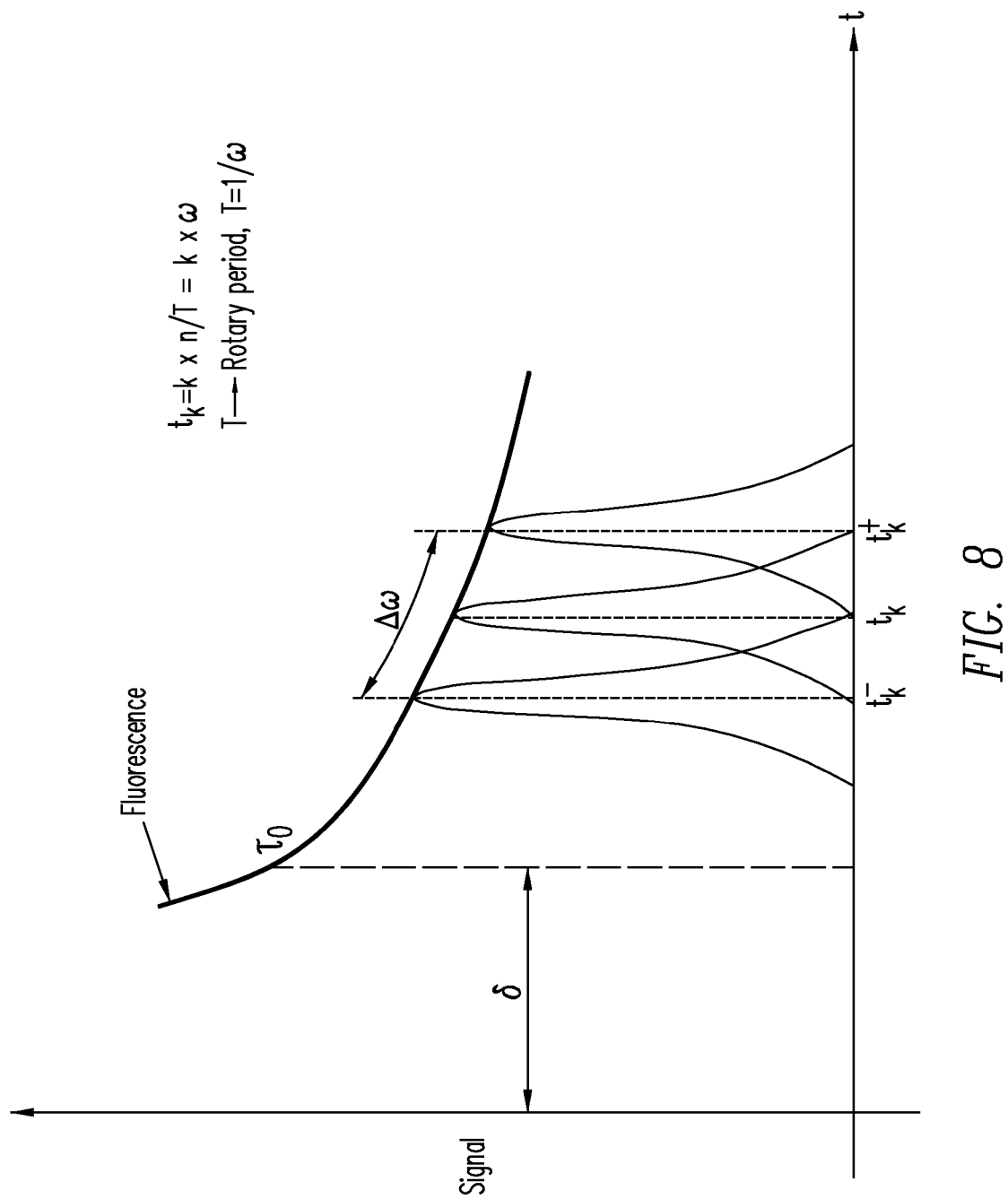
FIG. 8 shows the theoretical time-profile of the fluorescence signal in a single optical channel of the device, as it would appear when performing the step-speed-scan algorithm for lifetime measurements.

Another embodiment of the instrument comprises a discrete Laplace transform algorithm, used to measure the different lifetimes and concentrations, $\{\tau_i\}$ and $\{\zeta_i\}$ in Eq. (1). This algorithm is illustrated in FIG. 8. The method of using a Laplace transform to deconvolve Eq. (1) in terms of $\{\chi_i\}$ and $\{\tau_i\}$ has been well-known for a number of years (See M. Ameloot, J. M. Beechem, L. Brand; "Simultaneous Analysis of Multiple Fluorescence Decay Curves By Laplace Transforms", Biophysical Chemistry 23, 155171 (1986)). In the case of a RadiaLight® based instrument, two modifications are necessary: a discrete transform process has to be implemented, and also a time delay $\delta$ needs to be considered between the pump pulse and the start of signal collection. Equations (9.1-3) show the three discrete functions that will be of relevance.

$$I_k = \sum_i \zeta_i e^{-t_k/\tau_i} \tag{9.1}$$

$$\frac{dI_k}{dt_k} = -\sum_i \frac{\zeta_i}{\tau_i} e^{-t_k/\tau_i} \tag{9.2}$$

$$\frac{d^2 I_k}{dt_k^2} = \sum_i \frac{\zeta_i}{\tau_i^2} e^{-t_k/\tau_i} \tag{9.3}$$

Eq. (9.1) is proportional to the intensity measured by the k-th channel of the RadiaLight® switch, and Eqs. (9.2) and (9.3) are its successive time derivatives. Throughout this discussion, a sample with three different species will be used for calculations and examples. Any person skilled in the art will recognize that the technique can be extended to a sample with any number K of components. FIG. 8 shows the basic principle for the step-speed scan technique. In FIG. 8, a single channel fluorescence signal is shown for different values of the rotational speed $\omega$ of the device. Here, the device is operated at a central speed $\omega_0$ for one complete cycle. The speed is then increased to a value $\omega^-$, and a new set of measurements is collected through another cycle.[1] This is followed by a new cycle scan measurement, where the speed of the device is reduced to $\omega^+$.

[1] The choice of '−' superscript is based on the fact that, whereas, $\omega^+ < \omega_0 < \omega^-$, also, $t_k^- < t_k < t_k^+$.

With the measurements performed in this manner, the first and second time derivatives of the intensity can be collected, for every channel in the device, as follows, $$\frac{dI_k}{dt_k} = \tag{10}$$

$$\left(\frac{1}{2}\right) \cdot \left(\frac{I_k^+ - I_k}{\Delta t_k^+} + \frac{I_k - I_k^-}{\Delta t_k^-}\right) = \frac{1}{2\pi} \frac{\omega n}{\Delta \omega k}(\omega^+(I_k^+ - I_k) + \omega^-(I_k - I_k^-)),$$

$$\frac{d^2 I_k}{dt_k^2} = \left(\frac{2}{t_k^+ - t_k^-}\right) \cdot \left(\frac{I_k^+ - I_k}{\Delta t_k^+} - \frac{I_k - I_k^-}{\Delta t_k^-}\right) =$$

$$\frac{2}{\pi^2}\left(\frac{\omega n}{\Delta \omega k}\right)^2 \left(\frac{\omega^+ \omega^-}{\Delta \omega}\right) \cdot (\omega^+(I_k^+ - I_k) - \omega^-(I_k - I_k^-)).$$

On the other hand, the optical power intensity $I(t)$, measured by the photo-detector as the RadiaLight® switch cycles through the channels, is a function of time to which a Laplace transform can be applied, with the following result, $$L_S(I) = \int_0^\infty e^{-st} I(t) dt, \tag{11}$$

$$I(t) = \sum_k I_k \delta(t - t_k),$$

$$\Rightarrow L_S(I) \cong \sum_k \sum_i \zeta_i \int_{t_k - \Delta_k/2}^{t_k + \Delta_k/2} e^{-(s + 1/\tau_i)t} dt$$

$$\cong \sum_k \sum_i \zeta_i e^{-st_k} \frac{e^{-t_k/\tau_i}}{\left(s + \frac{1}{\tau_i}\right)} \cdot \left((s + 1/\tau_i)\Delta_k - \left(s + \frac{1}{\tau_i}\right)^2 \frac{\Delta_k^2}{2} + \left(s + \frac{1}{\tau_i}\right)^3 \frac{\Delta_k^3}{6}\right)$$

$$= \sum_k \sum_i \zeta_i e^{-st_k} \cdot e^{-t_k/\tau_i} \cdot \left(\left(\Delta_k - s \cdot \frac{\Delta_k^2}{2} + s^2 \cdot \frac{\Delta_k^3}{6}\right) - \frac{1}{\tau_i} \cdot \left(\frac{\Delta_k^2}{2} - s \frac{\Delta_k^3}{3}\right) + \frac{1}{\tau_i^2} \cdot \frac{\Delta_k^3}{6}\right)$$

$$= \sum_k e^{-st_k} \left\{I_k \cdot P_2^k(s) + \frac{dI_k}{dt_k} \cdot P_1^k(s) + \frac{d^2 I_k}{dt_k^2} \cdot P_0^k(s)\right\},$$

where the following definitions apply, $$\delta(t - t_k) = \begin{cases} 1, & t_k - \Delta_k/2 < t < t_k + \Delta_k/2 \\ 0, & \text{otherwise} \end{cases}$$

$$\Delta_k = t_{k+1} - t_k, \quad P_0^k(s) = \frac{\Delta_k^3}{6}, \quad P_1^k(s) = \frac{\Delta_k^2}{2} - s \frac{\Delta_k^3}{3},$$

-continued $$P_2^k(s) = \Delta_k - s \cdot \frac{\Delta_k^2}{2} + s^2 \cdot \frac{\Delta_k^3}{6},$$

and use has been made of the definitions in Eq. (9). The right hand side in Eq. (11) comprises a sum of terms that can be obtained by direct, discrete measurement with the RadiaLight® device, using the supplementary functions of the parameter s, shown above. These functions (the polynomials, $P_i^k$, and an exponential) include factors that involve knowledge of $t_k$ at every point of the measurement, which is also a given in the RadiaLight® architecture. The functions $I_k'$ and $I_k''$ can also be obtained from measurement, as shown in FIG. 8, and Eq. (10); in this case, knowledge of $t_k$ is necessary at three different points for each channel k and measurements at three different values of ω are also needed. Overall, evaluation of the right-hand side of Eq. (11) requires measurement of $I_k$ at three different speeds, and the collection of (ω, ω$^+$, and ω$^-$), and ($t_k$, $t_k^+$, $t_k^-$). This means that, for each measurement, at least three complete cycles of the RadiaLight® switch will be needed, for a total of 3k+6 parameters. Furthermore, the number of cycles needed to complete a measurement may be larger, as will be shown below.

A calculation of the Laplace transform of a continuous fluorescence decay function renders the following result, $$L_S(I) = \int_0^\infty e^{-st} I(t)dt, \quad (12)$$

$$I(t) = \sum_i \zeta_i e^{-t/\tau_i},$$

$$\Rightarrow L_S(I) = \sum_i \frac{\zeta_i}{\left(s + \frac{1}{\tau_i}\right)}.$$

Equation (12) is a rational function of polynomials, with parameters, $\{\zeta_i\}$, and, $\{\tau_i\}$. These functions are readily suitable for nonlinear curve fitting by any standard method available, e.g. Levenberg-Marquardt routines. The procedure is to equate the right hand side of Eq. (12) to the right hand side of Eq. (11). Once this is done, then the nonlinear curve fitting can be implemented to the data processed as described in the right hand side of Eq. (11), in order to extract the parameters $\{\zeta_i\}$ and $\{\tau_i\}$ altogether. However, we need to realize that the RadiaLight® switch operates in such a manner that there will always be a time-gap δ between the optical pumping and the start of the measurement, as shown in FIG. 8. Even though the simplest realization of the RadiaLight® device implies that δ=$t_1$, in the following we will treat δ as an independent parameter that can be adjusted by special design of the instrument. The issue will be to see what values of δ are permissible so that the model can accurately predict $\{\zeta_i\}$ and $\{\tau_i\}$ for a given sample. The starting point is to replace the integral in Eq. (12) by a modified Laplace transform $L_s^\delta(I)$ as follows:

$$L_s^\delta(I) = \int_\delta^\infty e^{-st} I(t)dt, \quad (13)$$

$$I(t) = \sum_i \zeta_i e^{-t/\tau_i},$$

-continued $$\Rightarrow L_s^\delta(I) = \sum_i \zeta_i \left\{ \frac{1}{\left(s + \frac{1}{\tau_i}\right)} - \delta + \left(s + \frac{1}{\tau_i}\right) \cdot \frac{\delta^2}{2} \right\}.$$

The key assumption of the proposed methodology is then:

$$\sum_i \zeta_i \left\{ \frac{1}{\left(s + \frac{1}{\tau_i}\right)} - \delta + \left(s + \frac{1}{\tau_i}\right) \cdot \frac{\delta^2}{2} \right\} = \quad (14)$$

$$\sum_k e^{-st_k} \left\{ I_k \cdot P_2^k(s) + \frac{dI_k}{dt_k} \cdot P_1^k(s) + \frac{d^2 I_k}{dt_k^2} \cdot P_0^k(s) \right\}.$$

Figure 9:
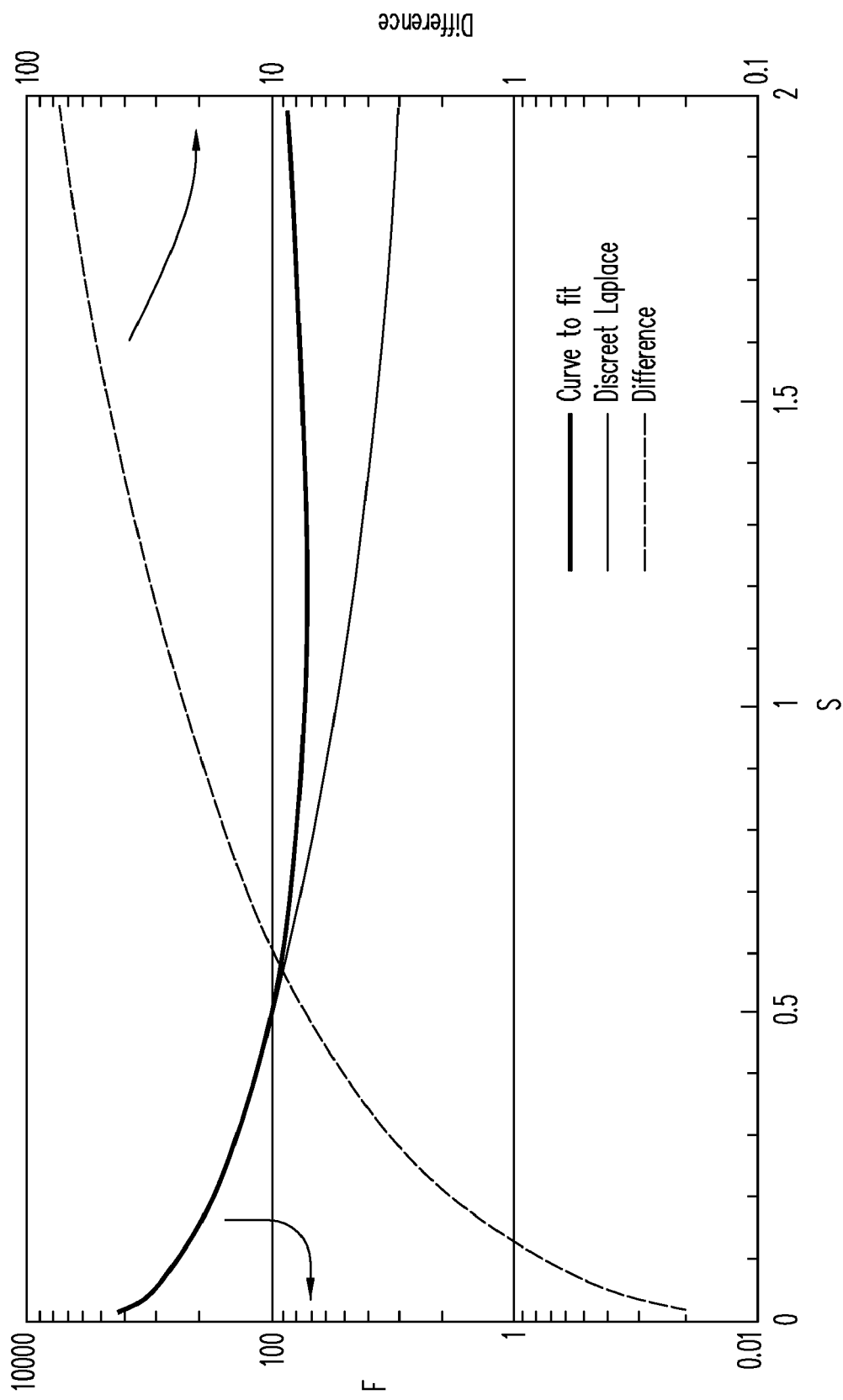
FIG. 9 shows the difference between curve to fit (Eq. (14), left-hand side), and discrete Laplace Transform (Eq. (14), right hand side), using a RadiaLight® TRF spectrometer with 100 channels, ω=5×10⁵ (RPM). S is the Laplace parameter. The sample considered has $\{\zeta\}$=(10, 30, 70), and $\{\tau\}$=(30, 50, 10) μsec.

The validity of Eq. (14) occurs for only a given range of values of s. FIG. 9 shows a plot of the two sides of Eq. (14), for δ=τ=1.2 μsec. The important point is to perform the nonlinear fit in a region for small enough s, so that the equality of the two sides of Eq. (14) is maintained with sufficiently good precision. Also, notice that the left-hand side of Eq. (14) is obtained assuming integration over an infinite time interval. What this means is that the longer the RadiaLight® device polls the signal channels after a given pump pulse, the more accurate Eq. (14) will be. Therefore, multiple measurement cycles may be needed after a pump pulse is delivered. This is in addition to the three cycles at different speeds that the discrete scheme requires, in order to obtain a measurement.

Figure 10:
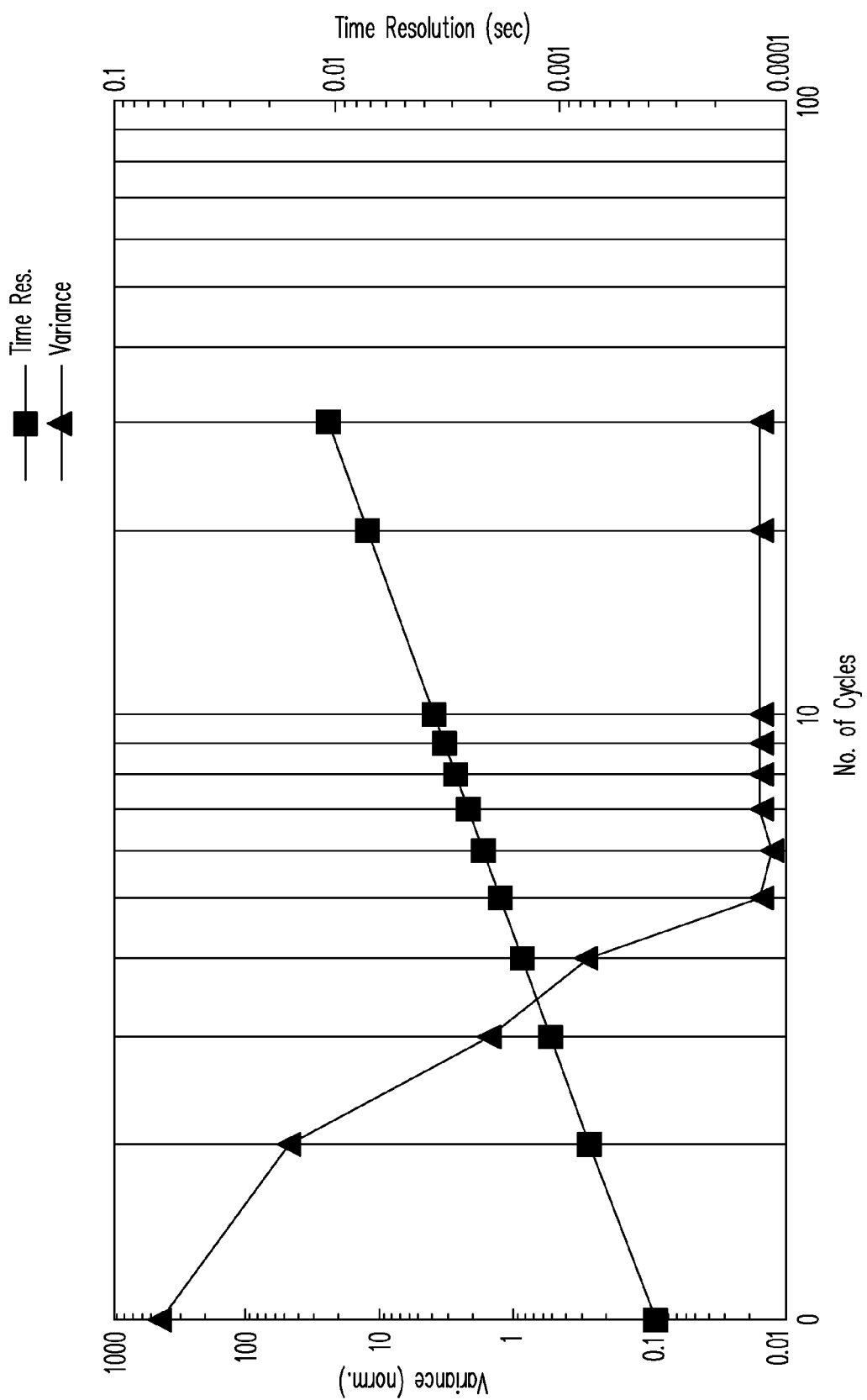
FIG. 10 plots variance and time resolution as a function of the number of cycles per measurement. The values of $\{\overline{\zeta}_m\}$, $\{\overline{\tau}_m\}$, and ω, are as in FIG. 9, above. Note that even for 30 cycles, the overall time resolution is well below 100 ms.
Figure 11:
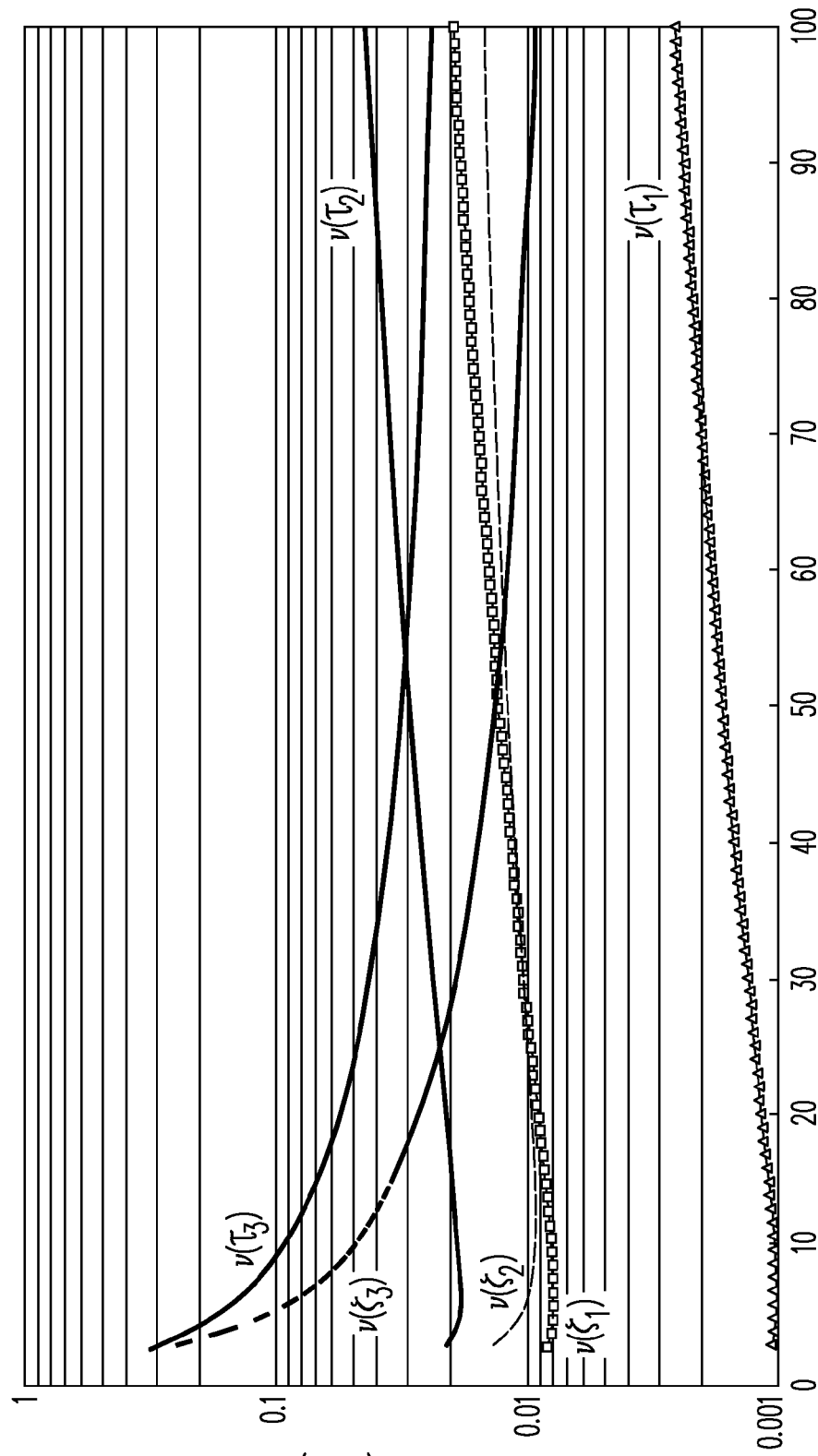
FIG. 11 shows the variance of all six parameters, $\{\overline{\zeta}_m\}$, $\{\overline{\tau}_m\}$, as the concentration $\zeta_1$ of analyte 1 is varied. Most of the values lie in the 2-4% variance range.

For a quantitative analysis, we define here a variance of the measurement, or goodness of fit, ν, as follows:

$$\nu = \frac{1}{2M} \sqrt{\sum_m \left(\frac{\zeta_m - \overline{\zeta}_m}{\overline{\zeta}_m}\right)^2 + \left(\frac{\tau_m - \overline{\tau}_m}{\overline{\tau}_m}\right)^2}, \quad (15)$$

where, M, is the total number of analytes to be measured in the sample (3, for the present example), and $\{\overline{\zeta}_m\}$, $\{\overline{\tau}_m\}$, are the actual values of concentration and lifetime for the sample. FIG. 9 shows how sensitive the value of ν is, with respect to the number of cycles in a measurement. Once the low-variance limit is reached, any further increase in cycling will no longer produce better results. The precise value at which this condition is attained depends strongly on the specific values of the true parameters $\{\overline{\zeta}_m\}$ and $\{\overline{\tau}_m\}$. FIG. 10 also shows the time resolution of the measurement for the different cycles used, including a factor of 3, to account for the step-speed scan. For the center speed used in the calculation (ω=5×10$^5$ RPM), it is seen that cycling the instrument up to 30 times per measurement results in a time resolution of about 10 ms. FIG. 11 shows the correlation of the variances between the different parameters, as the concentration of analyte 1 changes. Correlation is high, but variances are kept below 5% across a wide range of values for $\zeta_1$.

Algorithm No. 4.

Figure 12A:
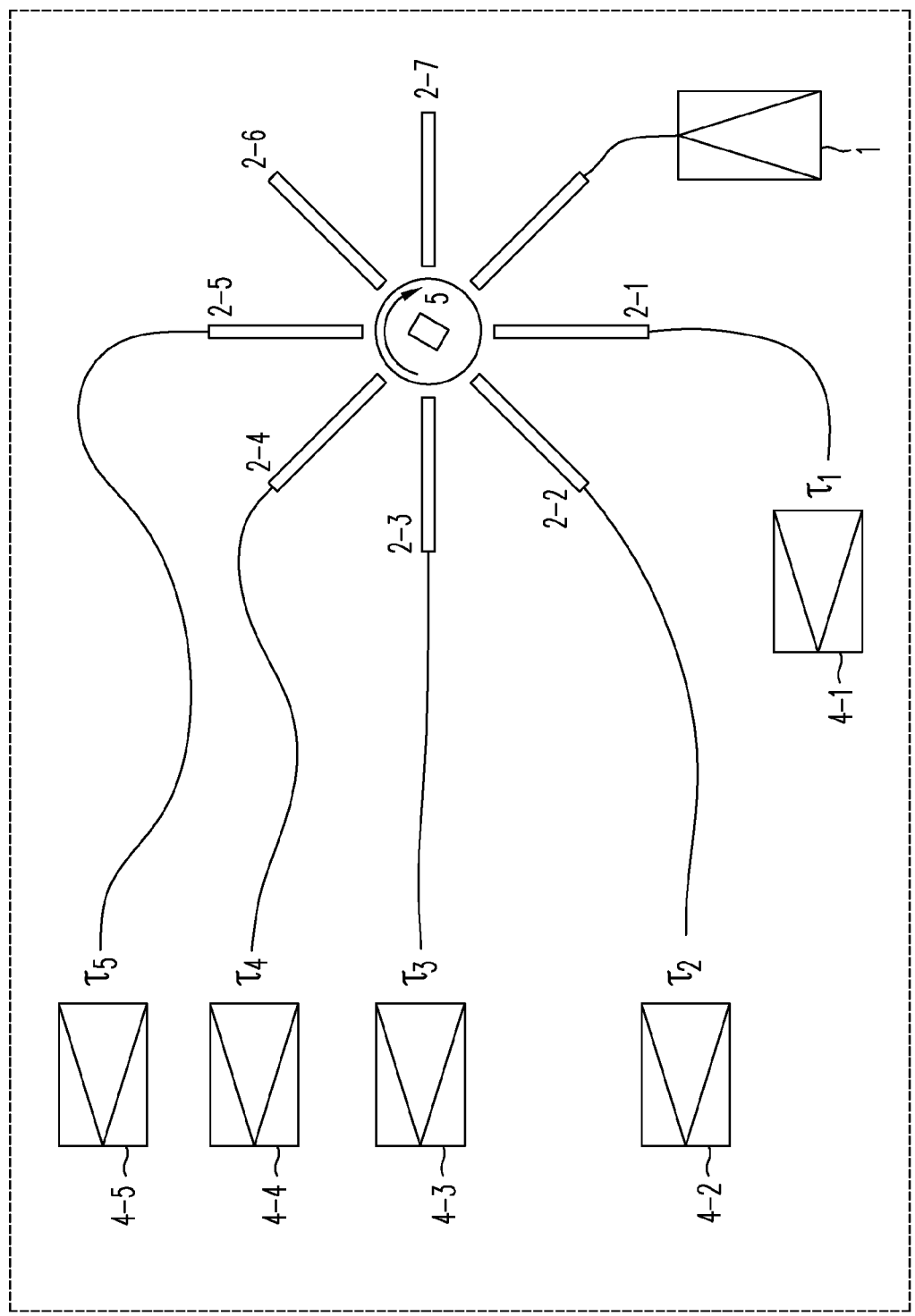
FIG. 12 (a) shows a structure using separate photodetectors 4-1 to 4-7 (photodetectors 4-6 and 4-7 are not showing) for each channel 2-1 to 2-7 shown to perform a continuous speed-scan measurement of a time-resolved fluorescence spectrum. Notice that, in this configuration, each channel in the RadiaLight® device uses a different photodetector 4-$i$. Elements in FIG. 12a are numbered the same as corresponding elements in the structure of FIGS. 1a and 1b.
Figure 12B:
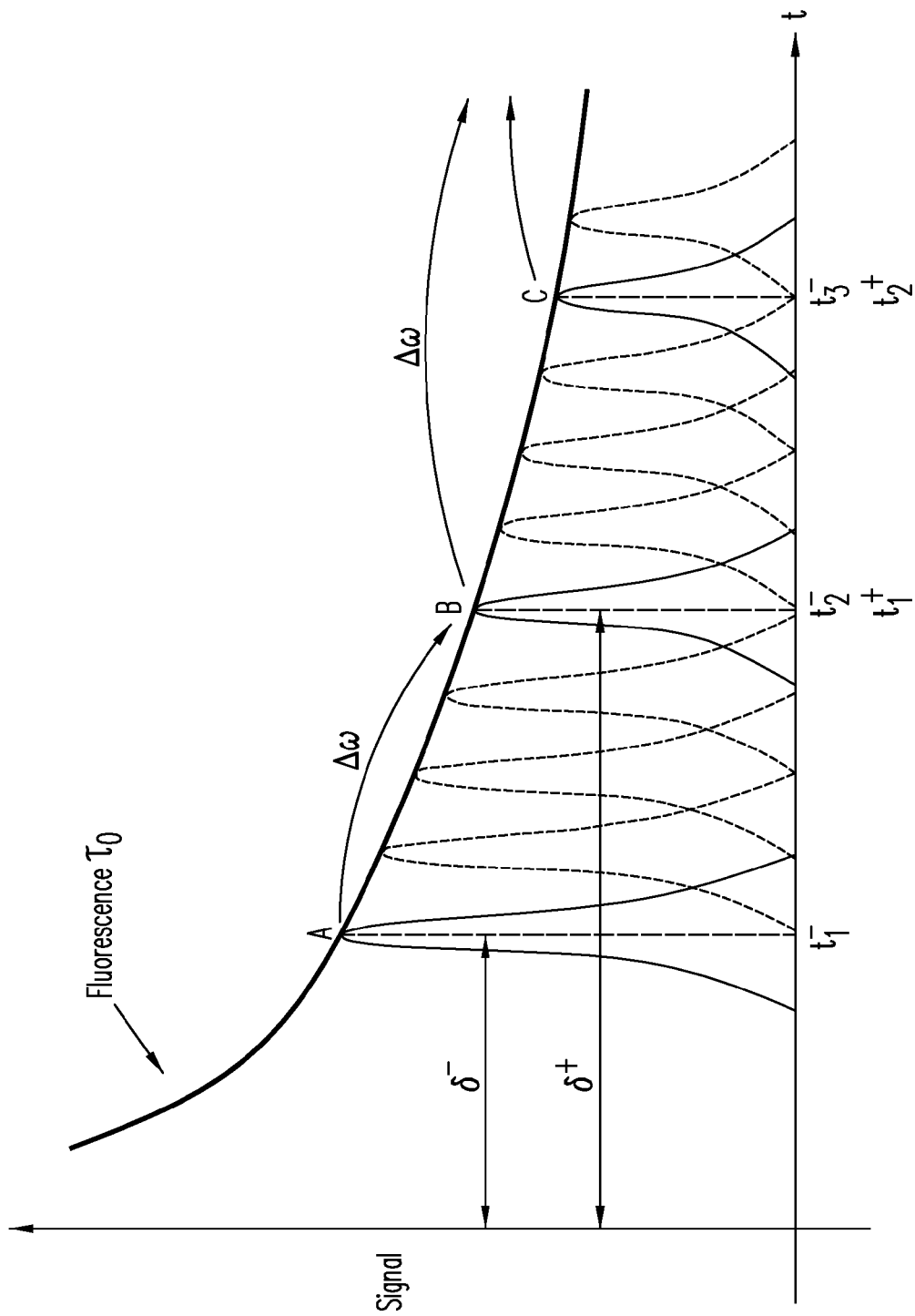

In another embodiment of the modified Laplace transform algorithm, a continuous speed scan method is applied. A structure for implementing this embodiment is illustrated in FIG. 12a and the waveform resulting from the use of the structure of FIG. 12a is shown in FIG. 12b. The concept in this case is to continuously change the speed of the RadiaLight® device 50 between two limiting values, ω$^+$<ω$^-$, while the power measured on each channel is monitored separately. FIG. 12a shows the structure used for the measurement. Shown in FIG. 12a is a rotating prism 5 with seven waveguides 2-1 through 2-7. Laser 1 provides a source of light to be incident on the sample (not shown in FIG. 12a but located relative to the structure in FIG. 12a as shown in FIGS. 1a and 1b). Notice that in the case of a continuous reduction of rotational speed, as the signal from any given channel slows down, the device may end up measuring a portion of the signal that had already been measured by a previous channel at an earlier time. As a result, different channels will end up polling overlapping regions of the time-decay fluorescence signal. This is illustrated in FIG. 12b. Because this could lead to confusion of the overall signal, each channel has to be monitored on a separate photo-detector 4-1 through 4-7 of which only photo-detectors 4-1 through 4-5 are shown.

Figure 13:
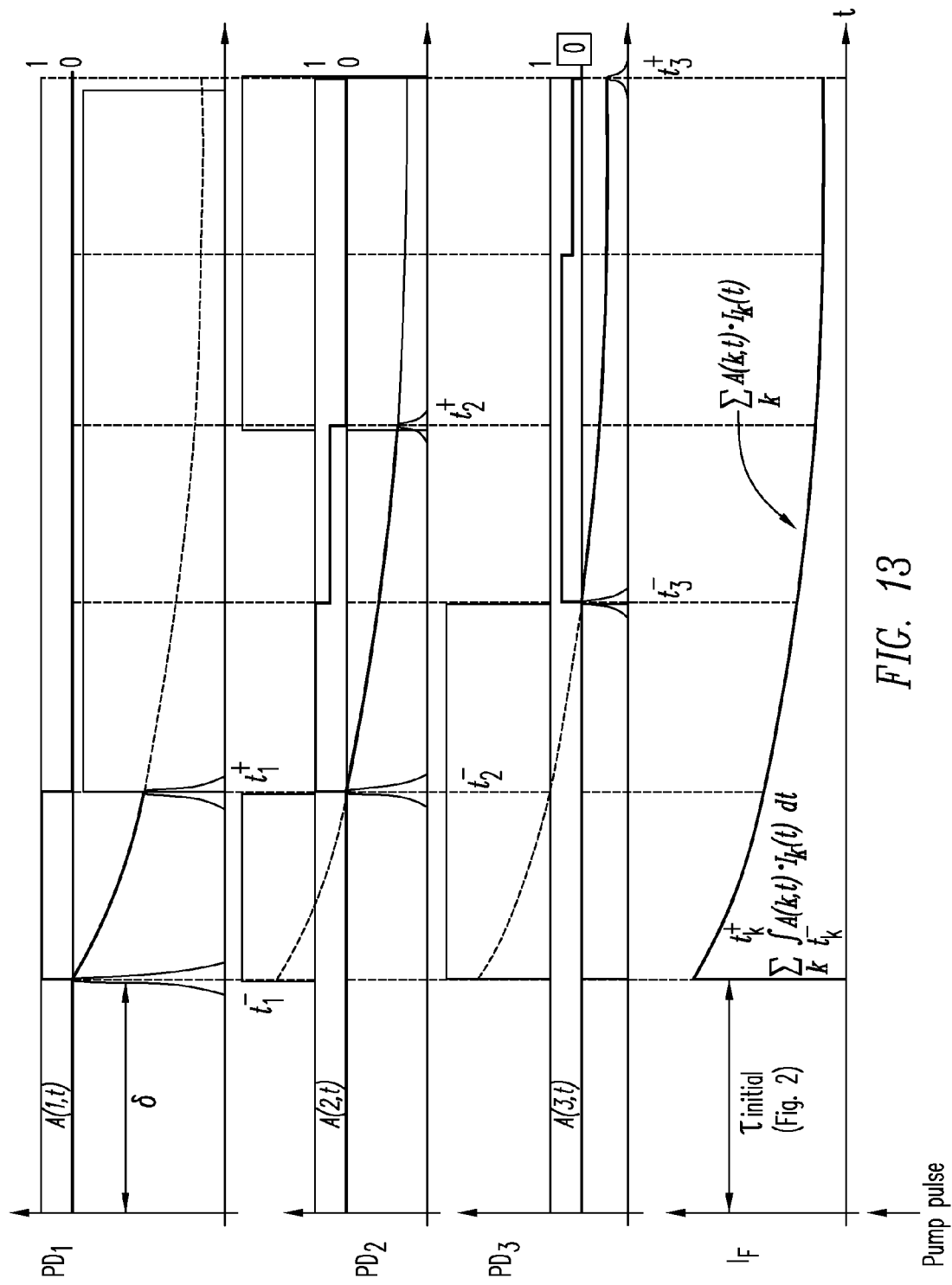
FIG. 13 shows schematically the time-profile measurements of each photo-detector from different channels in the RadiaLight® spectrometer, and how they result in the continuous speed scan technique to apply a Laplace transform algorithm. Note also the functions A(k, t), which take into account the overlapping in time of the different signals.

Anyone skilled in the art will recognize that other embodiments of the invention can be implemented by which this procedure can be avoided, if the signal from each channel is tracked and stored separately by some other electronic means. The process of computing the Laplace transform using the signal coming from each photo-detector and ad-hoc overlap-counting functions, A(k, t), is illustrated in more detail in FIG. 13. For illustrative purposes, in FIG. 13 the initial and final rotational speed of the instrument are such that the first channel winds up at the time slot position that the second channel occupied in the initial configuration. The end result of this process is that a continuous Laplace transform is applied to the function $I_F(t)$, starting at an initial time, $\delta \neq 0$, as will be disclosed below. Notice that, from FIG. 13:

$$I_F(t) = \sum_k A(k, t) \cdot I_k(t)$$

Equation (16) shows the calculation procedure to find the coefficients $\{\zeta\}$, and $\{\tau\}$. The right hand side is the result of the measurement, where the coefficient A(k,t) takes care of the overlap between the integrals for the different channels. This overlap factor depends on the channel number, and also on the specific time interval considered. The left-hand side contains the formula and the parameters upon which the nonlinear regression is applied.

$$L_s^\xi(I) = \qquad (16)$$

$$\sum_i \zeta_i \left\{ \frac{1}{\left(s + \frac{1}{\tau_i}\right)} - \delta + \left(s + \frac{1}{\tau_i}\right) \cdot \frac{\delta^2}{2} \right\} = \sum_k \int_{t_k^-}^{t_k^+} A(k, t) e^{-st} I_k(t) dt$$

In practice, the overlap renders an averaged value of the signal during a certain time interval; this improves the signal-to-noise ratio (SNR) of the device. Once the range of speeds and the number of channels is known ($\omega^+$, $\omega^-$, and k), the coefficients A(k, t) can be easily determined. An example is the case illustrated in FIG. 12b. The speeds, $\omega^+$, and, $\omega^-$, are such that the first channel ends up being polled at time, $t_1^+ = t_2^-$, so that the overlap between channels 1 and 2 is exactly zero. For a simple case with k=8 optical channels in the RadiaLight® switch, the values of the A(k,t) coefficients are listed in Table 1. Notice that the sum across each row is equal to 1, to ensure that the fluorescence decay measurement during any given time-interval is only counted once.

| | A(1, t) | A(2, t) | A(3, t) | A(4, t) | A(5, t) | A(6, t) | A(7, t) | A(8, t) |
|---|---|---|---|---|---|---|---|---|
| $(t_1^-, t_2^-)$ | 1 | | | | | | | |
| $(t_2^-, t_3^-)$ | | 1 | | | | | | |
| $(t_3^-, t_4^-)$ | | ½ | ½ | | | | | |
| $(t_4^-, t_5^-)$ | | | ½ | ½ | | | | |
| $(t_5^-, t_6^-)$ | | | ⅓ | ⅓ | ⅓ | | | |
| $(t_6^-, t_7^-)$ | | | | ⅓ | ⅓ | ⅓ | | |
| $(t_7^-, t_8^-)$ | | | | ¼ | ¼ | ¼ | ¼ | |
| $(t_8^-, t_5^+)$ | | | | | ¼ | ¼ | ¼ | ¼ |
| $(t_5^+, t_6^+)$ | | | | | | ⅓ | ⅓ | ⅓ |
| $(t_6^+, t_7^+)$ | | | | | | | ½ | ½ |
| $(t_7^+, t_8^+)$ | | | | | | | | 1 |

Figure 14:
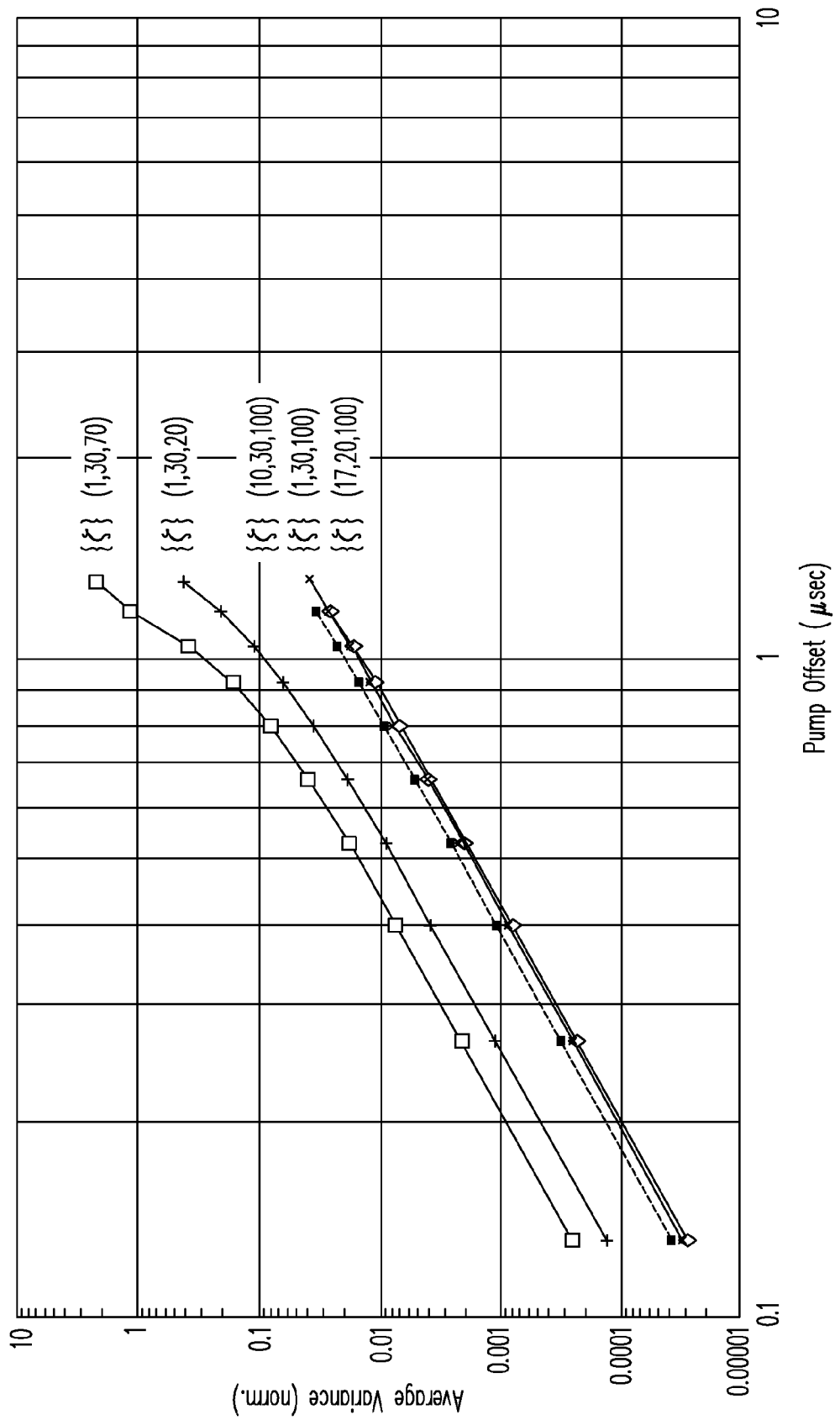
FIG. 14 shows the average variance resulting from a continuous speed-scan algorithm (Eq. 16). The variance is calculated using Eq. (15), and the variable parameter is the pump offset, δ (see FIG. 11). The samples simulated for each curve contain different sets of concentrations, $\{\zeta_i\}$, and $\{\tau_i\}$={10, 60, 100} μs.

FIG. 14 shows the result of a simulation following the procedure outlined in Eq. (16), for different sets of $\{\zeta_i\}$, and $\{\tau_i\}=\{10, 60, 100\}$ µs. The variance is calculated as in Eq. (15), and the variable parameter is the pump offset 6.

The invention disclosed herein can be used in a number of applications. In the following, some applications where the present invention can be used will be described in detail. This set of applications is not limiting, and anyone skilled in the art will recognize that the present invention can be applied to many other areas where time-resolved fluorescence spectroscopy is of relevance. We first realize that the present invention will be useful with fluorescence processes with decay lifetimes that are about 1 µs or longer although the present invention can also be used with fluorescence processes with shorter decay lifetimes. Table II shows a list of ligands (L) that can be attached to Rhenium-based complexes, to produce fluorescent molecules with different decay lifetimes, as shown. "MLC" stands for metal ligand complexes.

TABLE II

| L | Quantum Efficiency (η) | Lifetime (µs) |
|---|---|---|
| Cl⁻ | 0.005 | 0.051 |
| 4-NH$_2$Py | 0.052 | 0.129 |
| Py | 0.16 | 0.669 |
| CH$_3$CN | 0.41 | 1.201 |

Fluorescence properties of Re-based, metal-ligand complexes. L - stands for the "ligand" that is attached to the Re complex. The ligand essentially changes the non-radiative lifetime of the complex, therefore inducing a change in, η, and, τ. Source: J. R. Lakowicz; Principles of Fluorescence Spectroscopy, 2nd Edition, Kluwer Academic/Plenum Publishers, New York (1999). ISBN: 0-306-46093-9.

Figure 15:
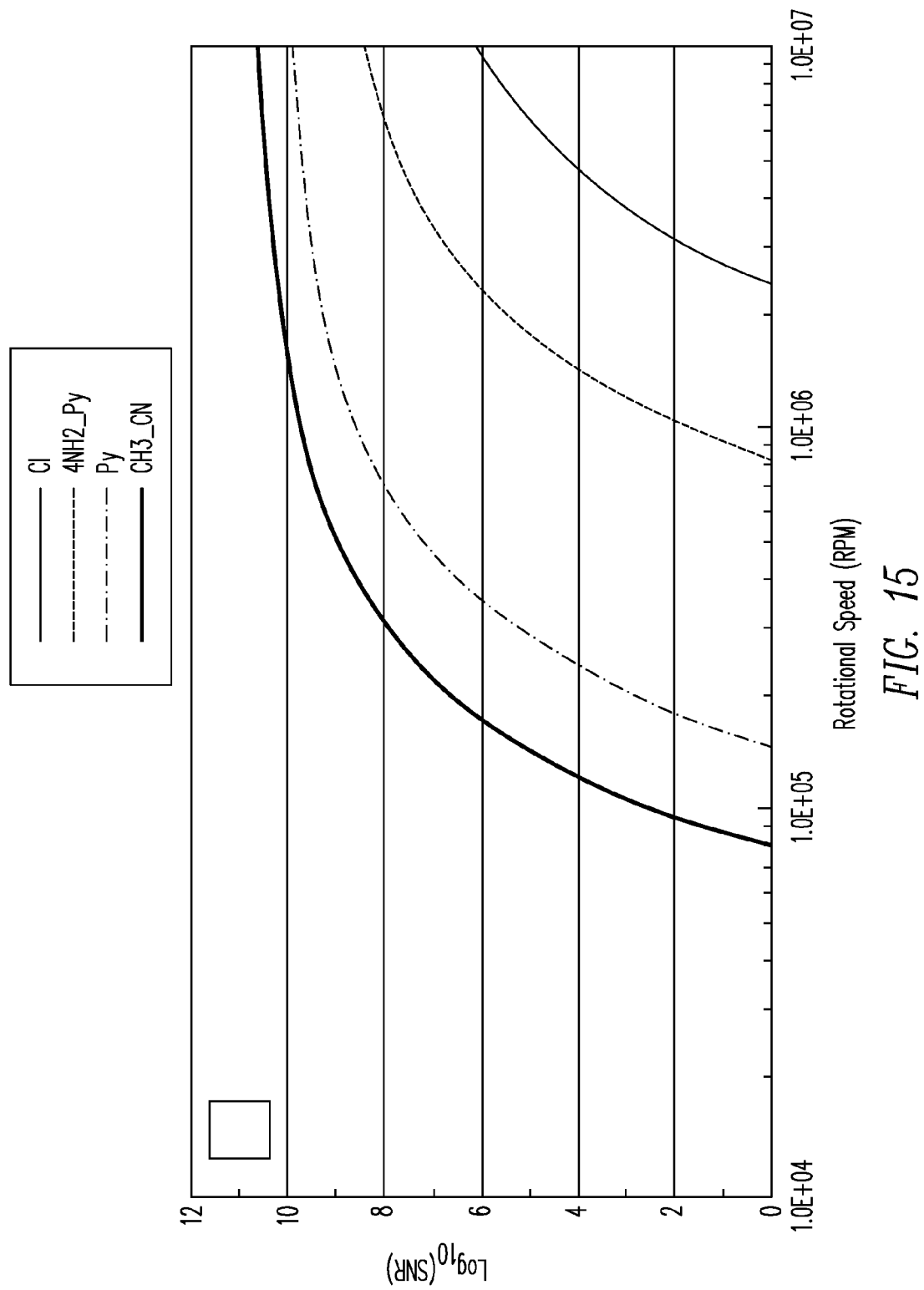
FIG. 15 shows the SNR in the photodetector of the RadiaLight® spectrometer obtained for the four different fluorophores listed in Table II, as a function of the rotational speed, ω. The instrument needs to be operated at speeds such that SNR>1 for all samples of interest.

To carry out in the devices described herein the analysis described and the algorithms disclosed in the present invention, it is crucial to determine the operational specifications of the devices so that the signal-to-noise ratio (SNR) allows for a meaningful result. Using the device of FIG. 1a, consider the average value of the signal during the passage of the beam from the reflecting element 5 through a single optical channel (e.g. 2-1). The signal-to-noise ratio (SNR) of the instrument is determined by the value of the average signal on a single channel, the noise-equivalent-power (NEP) of the photodetector, and the measurement bandwidth, B=1/ΔT. A state-of-the-art photodetector can reach NEP values of 1 fW/√Hz. Using this as a benchmark value, FIG. 15 shows the SNR plots for the four Re-based, MLCs from Table II, as a function of ω. For the specific choice of fluorophore concentration ($\chi=1\times10^{-6}$ Mol/l) and input pump power (100 mW), a rotational speed of about $3\times10^6$ RPM would be necessary in order to accurately measure all four complexes simultaneously, in a given sample (SNR≧1). A rotating reflective element 5 can be fabricated using micro-electric-mechanical system (i.e. MEMS) technology. Devices that achieve a rotational speed of several million RPM's have been demonstrated in the past few years (see Luc G. Frechette, Stuart A. Jacobson, Kenneth S. Breuer, Fredric F. Ehrich, Reza Ghodssi, Ravi Khanna, Chee Wei Wong, Xin Zhang, Martin A. Schmidt and Alan H. Epstein; "Demonstration of a micro fabricated high-speed turbine supported on gas bearings" Solid-State Sensor and Actuator Workshop, Hilton Head Is., SC, Jun. 4-8, 2000).

Another application of the presently disclosed invention is in the field of fluorescence polarization immunoassays (FPIs). FPIs are commonly used in drug manufacturing processes and in clinical analysis. The task is to measure the polarization anisotropy of a given sample that has been tagged with some fluorescence material and has been mixed with a specific antibody. The polarization anisotropy of the sample depends strongly on the relative concentration of the target molecule, and target-antibody complexes. However, in the case of large antigen targets, the change in anisotropy with target concentration is significant only for fluorescent tags that have long lifetimes, (few 100's of ns to a few μs). For this type of molecule (with molecular weight in the order of tens of 1000's of Daltons), only long-lived MLC's can be used as fluorescent tags. For this reason, the time-resolved fluorescence spectrometer disclosed herein is an ideal device for FPI measurements.

Another application of the time-resolved fluorescence spectrometer disclosed herein is for an oxygen sensing device. Measurement of oxygen has relevance in applications as diverse as combustion process monitoring, semiconductor manufacturing, and blood gas measurement for clinical purposes. Anyone skilled in the art will realize that the use of the presently disclosed devices for oxygen sensing is not limited to the above mentioned applications, but can be extended to any other situation or configuration in which there is a need for measuring oxygen concentrations in a given fluid (liquid or gas) accurately and in a short period of time.

Fluorescence-based $O_2$ sensors make use of the quenching of a luminescent species by molecular oxygen. The luminescence intensity and decay lifetime become a function of the oxygen concentration $[O_2]$, as described by the Stern-Volmer expression[2] (Equation 17).

Figure 16:
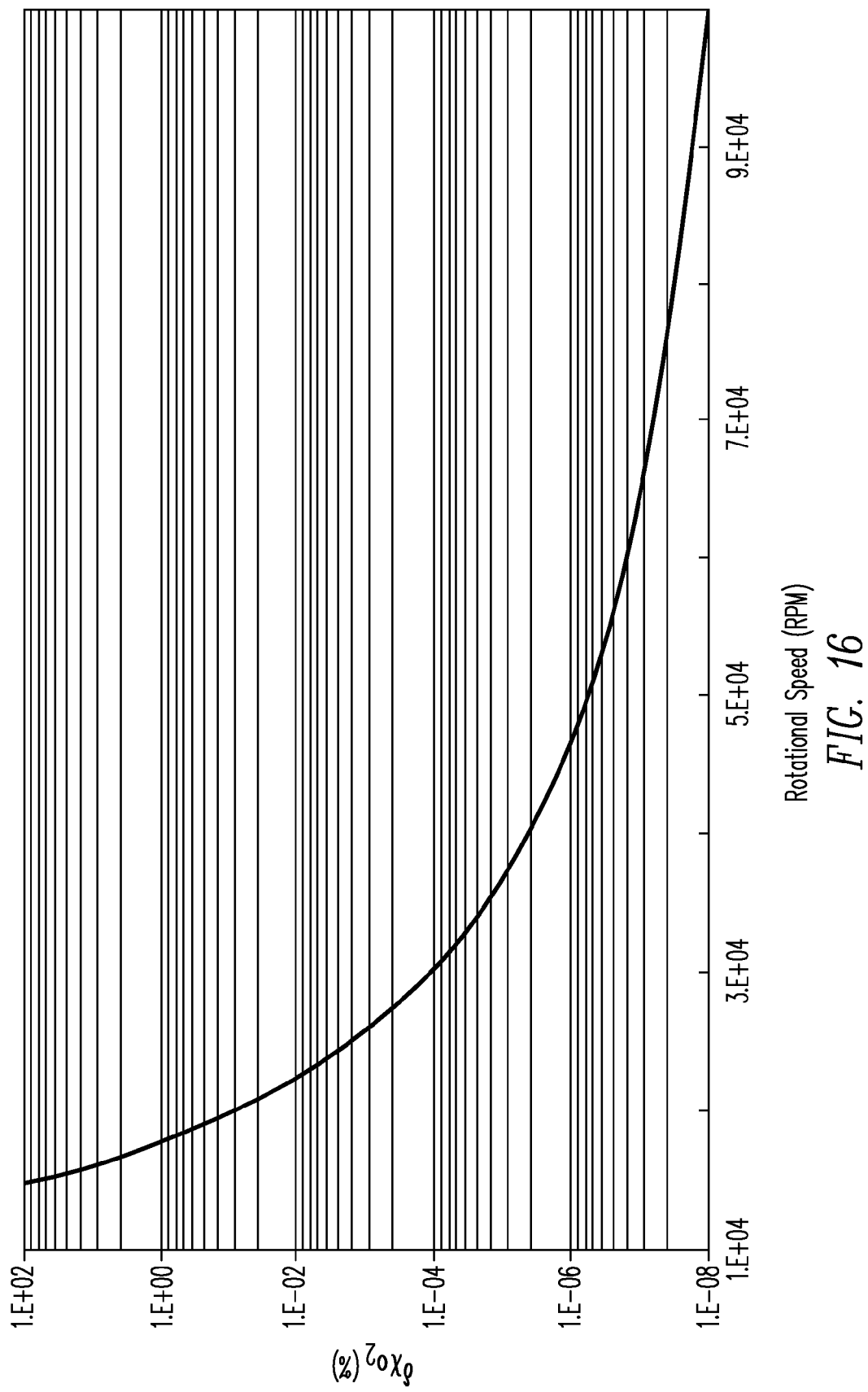
FIG. 16 shows the sensitivity in the measurement of $O_2$ (Eq. 18), as a function of the rotational speed, ω, of the device. The values in the Y-axis represent $O_2$ gaseous concentration.

[2] See: R. N. Gillanders, M. C. Tedford, P. J. Crilly, R. T. Bailey; "A composite sol-gel/fluoropolymer matrix for dissolved oxygen optical sensing", J. Photochem. Photobiol. A 163, 193-199 (2004).

$$\frac{I_0}{I} = 1 + K_{SV}[O_2] = 1 + k_q \tau_0 [O_2]. \quad (17)$$

where $I_0$ is the emission intensity in the absence of $O_2$, I is the emission intensity in the presence of $O_2$ at concentration $[O_2]$ (in %), $K_{SV}$ is the Stern-Volmer quenching constant, $k_q$ is the bimolecular quenching constant, and $\tau_0$ is the luminescence lifetime in the absence of $O_2$. The luminescent species selected is a Ruthenium poly-pyridil MLC, $[Ru(dpp)_3]^{2+}$. The values for its photo physical constants (Eq. (17)) are shown in Table III. FIG. 16 shows a plot of the error in oxygen concentration measurement as a function of co, calculated from Eq. (17) as $$\delta \chi_{O_2} = \frac{2}{\kappa} \cdot \frac{\delta I}{I} = \frac{2}{\kappa} \cdot SNR^{-1}. \quad (18)$$

The device in FIGS. 1*a* and 1*b* could use a Mircomo model FAULHABER 06-20 DC brushless servomotor to achieve the rotational speeds required to achieve the results shown in FIG. 16.

It is important to note that the results in FIG. 16 relate to a gaseous sample of oxygen. In the case of blood gas measurements, the use of Henry's Law enables the calculation of the amount of dissolved oxygen that can be measured in a liquid sample. Anyone skilled in the art would realize that the SNR of the device also changes due to differences in the index of refraction, coupling efficiencies, aging of the mechanical elements, temperature and humidity. However, a 0.01% $O_2$ gas-phase concentration corresponds to ~100 ppb blood $O_2$ concentration. According to FIG. 16, this amount of oxygen could be measured using a RadiaLight® time-resolved fluorescence spectrometer with 25 channels, at a time resolution of better than 3 ms at about 25,000 RPM. Anyone skilled in the art would recognize that other gases and ions for important biomedical-clinical applications can also be measured using the structure shown in FIGS. 1*a* and 1*b*, like $CO_2$ and $H^+$.

TABLE III

| | $K_{SV}(O_2^{-1}(\%))$ | $K_q(O_2^{-1}(\%) s^{-1})$ | $\tau_0$ (μs) |
|---|---|---|---|
| $[Ru(dpp)_3]^{2+}$. | 0.121 ± 0.008 | (2.1 ± 0.15) × 10 | 5.64 ± 0.07 |

Another application of the time-resolved fluorescence spectrometer disclosed in the present document is for a copper ion sensor. In addition to gas sensing, metal ion sensors based on fluorescence quenching can also be envisioned. The essential ingredient here is the sensitivity of the luminescent MLC to binding with both cations, such as $H^+$, $Na^+$, $Ca^+$, $Cu^{2+}$, and anions such as $Cl^-$ and $H_2PO_4^-$. Those skilled in the art will realize that the time-resolved fluorescence spectrometer disclosed herein can be used to track and monitor the presence of these ions in the human body, including but not limited to the blood stream and/or specific tissue, like brain tissue, in real time. Furthermore, those skilled in the art will recognize that the instrument described herein can be used for tracking and monitoring the presence of any and all of the above mentioned ions dissolved in water streams and water containers of varied size, purpose, and use. For example, this invention can be used to assist in the control of a saline water environment for fish tanks or oceanographic studies, the control of water contamination in public supplies, the control of water pollution in treatment plants and natural springs and rivers.

Figure 17:
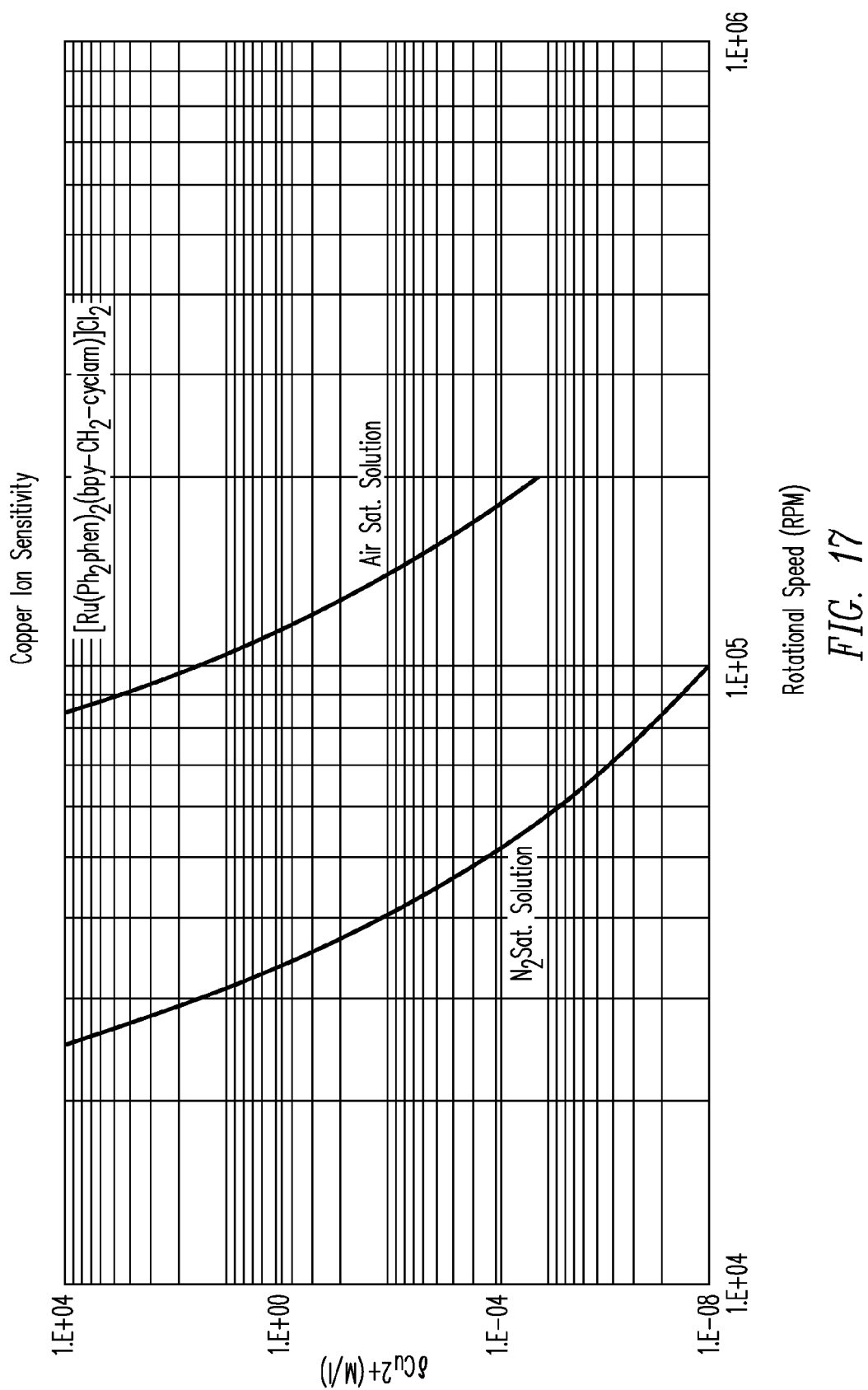
FIG. 17 shows the sensitivity in the measurement of $Cu^{++}$ as a function of the rotational speed, ω. Two curves are shown that represent different environmental conditions for the measurement. All relevant parameters are listed in Table IV.

Table IV lists the properties of a Ru-based complex that can be used as a copper ion sensor. (Taken from H. M. Rowe. W. Xu, J. N. Demas, B. A. DeGraff; "Metal Ion Sensors Based on a Luminescent Ruthenium (II) Complex): The Role of Polymer Support in Sensing Properties", Appl. Spectorsc. 56(2) 167-173 (2002)). FIG. 17 shows the results for a RadiaLight® fluorometer, with N=25 channels that uses this fluorophore. A concentration of $1 \times 10^{-8}$ M/l solution in $N_2$ saturated water corresponds to ~200 ppt (part per trillion) concentration. This can be measured at a rate of 0.6 ms (roundtrip) by the structure disclosed in FIGS. 1*a* and 1*b*.

TABLE IV

| [Ru(Ph$_2$phen)$_2$(bpy-CH$_2$-cyclam)]Cl$_2$ | Environment | $\tau_0$ (ns) | $K_{SV}$ (M$^{-1}$) |
|---|---|---|---|
| O$_2$ | Solution | 2300 | 7400 |
| Cu$^{2+}$ | Solution (N2 Saturated) | 2400 | 40 |
| Cu$^{2+}$ | Solution (Air Saturated) | 750 | 15 |

Other embodiments of this invention will be obvious to those skilled in the art in view of the above descriptions. For example, while non-fluorescent samples having fluorophores attached to them have been described as being used with the structures of this invention, samples which are intrinsically fluorescent can also be used with the structures of this invention. The above descriptions are meant to be illustrative and not limiting.

What is claimed is:

1. A fluorescence spectroscopy system comprising:
   a light source for producing light to be directed at a sample, said sample comprising at least one fluorophore:
   a time-division multiplexing device for taking Stokes radiation scattered from the sample as a result of said light impinging on said sample and distributing that Stokes radiation to each of a plurality of optical channels; and
   a detector for detecting the radiation carried by each of said optical channels;
   wherein each channel receives a signal from the sample during a portion of one cycle of said time division multiplexing device, said signal being detected by said detector;
   wherein said system includes a rotating prism for directing light from said light source to said sample and for directing fluorescent light from said sample to one or more of said plurality of light channels.

2. A fluorescence spectroscopy system comprising:
   a light source for producing light to be directed at a sample, said sample comprising at least one fluorophore;
   a time-division multiplexing device for taking Stokes radiation scattered from the sample as a result of said light impinging on said sample and distributing that Stokes radiation to each of a plurality of optical channels; and
   a plurality of detectors corresponding on a one-to-one basis with said plurality of optical channels for detecting the radiation carried by each of said optical channels;
   wherein each channel receives a signal from the sample during a portion of one cycle of said time division multiplexing device, said signal being detected by said detector.

3. The system as in claim 2 wherein said sample comprises a plurality of components and said system comprises a plurality of filters thereby to enable said system to detect substantially simultaneously said components in said sample.

4. A method of using a fluorescence spectroscopy system comprising:
   directing light at a sample, said sample comprising at least one fluorophore;
   taking Stokes radiation from the sample as a result of said light impinging on said sample and distributing at least a portion of said Stokes radiation to each of a plurality of optical channels using a time-division multiplexing device; and
   detecting the radiation carried by each of said optical channels;
   wherein each channel receives a signal from the sample during a portion of one cycle of said time division multiplexing device;
   wherein said time-division multiplexing device includes a rotating prism for directing light from said light source to said sample and for directing fluorescent light from said sample to one or more of said plurality of optical channels.

5. A method of using a fluorescence spectroscopy system comprising:
   providing a sample to be analyzed, said sample comprising at least one fluorophore;
   producing light from a light source to be directed at said sample;
   producing Stokes radiation as a result of said light impinging on said sample;
   distributing at least a portion of the Stokes radiation to each of a plurality of light channels;
   wherein distributing that Stokes radiation scattered from the sample to each of a plurality of optical channels comprises using a time-division multiplexing device, and
   wherein distributing that Stokes radiation scattered from the sample to each of a plurality of optical channels comprises causing each channel to receive a signal from the sample during a portion of one cycle of said time division multiplexing device;
   detecting the radiation carried by each of said optical channels; and further
   wherein detecting the radiation carried by each of said optical channels comprises using a plurality of detectors connected on a one-to-one basis to said plurality of optical channels.

6. The method of claim 5 wherein said sample comprises a plurality of components and said system comprises a plurality of filters thereby to enable said system to detect substantially simultaneously said components in said sample.

7. The method of claim 6 including analyzing the signal on each optical channel to identify a component in the sample.

8. The method of claim 6 wherein said signals are analyzed using fluorescence correlation spectroscopy.

9. The method of claim 6 wherein said signals are analyzed using fluorescence cross-correlation spectroscopy.

* * * * *